(12) United States Patent
Aston

(10) Patent No.: US 7,271,289 B2
(45) Date of Patent: *Sep. 18, 2007

(54) BIPHENYLCARBOXYLIC AMIDE DERIVATIVES AS P38 KINASE INHIBITORS

(75) Inventor: Nicola Mary Aston, Stevenage (GB)

(73) Assignee: SmithKline Beecham Corporation, Philadelphia, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/551,501

(22) PCT Filed: Apr. 7, 2004

(86) PCT No.: PCT/EP2004/003773

§ 371 (c)(1),
(2), (4) Date: May 25, 2006

(87) PCT Pub. No.: WO2004/089876

PCT Pub. Date: Oct. 21, 2004

(65) Prior Publication Data

US 2006/0241179 A1 Oct. 26, 2006

(30) Foreign Application Priority Data

Apr. 9, 2003 (GB) ................ 0308185.8

(51) Int. Cl.
C07C 233/65 (2006.01)
A61K 31/165 (2006.01)

(52) U.S. Cl. ............ 564/156; 564/175; 564/226; 544/133; 544/393; 514/311; 514/354; 514/363; 514/393; 514/408; 514/461; 514/522; 514/616; 514/252.12; 514/236.8

(58) Field of Classification Search ......... 514/311, 514/354, 363, 393, 408, 461, 522, 616, 252.12, 514/236.8; 544/133, 393; 546/175, 226; 548/127, 338.1, 567; 549/494; 558/414; 560/27; 564/147, 156, 146

See application file for complete search history.

(56) References Cited

U.S. PATENT DOCUMENTS

| | | | |
|---|---|---|---|
| 4,200,750 A | 4/1980 | Warner et al. | |
| 4,968,804 A | 11/1990 | Stanek et al. | |
| 5,064,832 A | 11/1991 | Stanek et al. | 514/256 |
| 5,236,934 A | 8/1993 | VanAtten | |
| 5,246,943 A | 9/1993 | Blankley et al. | |
| 5,521,213 A | 5/1996 | Prasit et al. | |
| 5,534,518 A | 7/1996 | Henrie et al. | |
| 5,658,903 A | 8/1997 | Adams et al. | |
| 5,858,995 A | 1/1999 | Kawai et al. | |
| 5,877,190 A | 3/1999 | Dhainaut et al. | |
| 5,932,576 A | 8/1999 | Anantanarayan et al. | |
| 5,945,418 A | 8/1999 | Bemis et al. | |
| 5,977,103 A | 11/1999 | Adams et al. | |
| 6,060,491 A | 5/2000 | Pruitt et al. | |
| 6,080,767 A | 6/2000 | Klein et al. | |
| 6,087,496 A | 7/2000 | Anantanarayan et al. | |
| 6,130,235 A | 10/2000 | Mavunkel et al. | |
| 6,147,080 A | 11/2000 | Bemis et al. | |
| 6,174,887 B1 | 1/2001 | Haruta et al. | |
| 6,251,914 B1 | 6/2001 | Adams et al. | |
| 6,277,989 B1 | 8/2001 | Chakravarty et al. | |
| 6,323,227 B1 | 11/2001 | Klein et al. | |
| 6,392,047 B1 | 5/2002 | Geissler et al. | |
| 6,399,627 B1 | 6/2002 | Song et al. | |
| 6,420,561 B1 | 7/2002 | Haruta et al. | 544/399 |
| 6,436,925 B1 | 8/2002 | Lubisch et al. | |
| 6,448,257 B1 | 9/2002 | Mavunkel et al. | 514/292 |
| 6,451,794 B1 | 9/2002 | Beswick et al. | |
| 6,498,166 B1 | 12/2002 | Campbell et al. | |

(Continued)

FOREIGN PATENT DOCUMENTS

EP 0 533 266 9/1992

(Continued)

OTHER PUBLICATIONS

Boehm et al., *Expert Opinion of Therapeutic Patents*, vol. 10 (1) pp. 25-37 (2000).
Boehm, et al, *Journal of Medicinal Chemistry*, vol. 39(20) pp. 3929-3937 (1996).
Ceccarelli et al., *European Journal of Medicinal Chemistry*, vol. 33 (12) pp. 943-955 (1998).
Gabriele et al., *European Journal of Organic Chemistry*, vol. 2001 (24) pp. 4607-4613 (2001).
Han et al., *Biohemica et Biophysica Acta—Molecular Cell Research*, vol. 1265 (2-3) pp. 224-227 (1995).

(Continued)

Primary Examiner—Shailendra Kumar
(74) Attorney, Agent, or Firm—Dara L. Dinner; Stephen Venetianer; Charles M. Kinzig

(57) ABSTRACT

Compounds of formula (I):

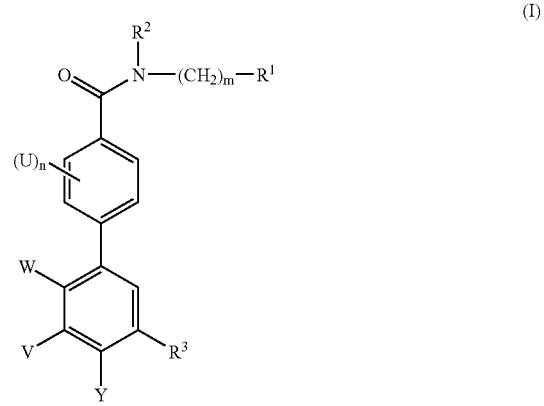

or pharmaceutically acceptable derivatives thereof, and their use as pharmaceuticals, particularly as p38 kinase inhibitors.

11 Claims, No Drawings

U.S. PATENT DOCUMENTS

| | | | |
|---|---|---|---|
| 6,509,361 B1 | 1/2003 | Weier et al. | |
| 6,509,363 B2 | 1/2003 | Salituro et al. | |
| 6,545,054 B1 | 4/2003 | Song et al. | 514/603 |
| 6,576,632 B1 | 6/2003 | Goldstein et al. | |
| 6,579,872 B1 | 6/2003 | Brown et al. | |
| 6,605,625 B2 | 8/2003 | Peukert et al. | |
| 6,638,980 B1 | 10/2003 | Su et al. | |
| 6,696,464 B2 | 2/2004 | McClure et al. | |
| 6,699,994 B1 | 3/2004 | Babu et al. | |
| 6,774,127 B2 | 8/2004 | Adams et al. | |
| 6,794,377 B2 | 9/2004 | Peukert et al. | |
| 6,821,965 B1 | 11/2004 | Brown et al. | |
| 6,855,719 B1 | 2/2005 | Thomas et al. | |
| 6,867,209 B1 | 3/2005 | Mavunkel et al. | 524/253 |
| 6,924,392 B2 | 8/2005 | Peukert et al. | 564/155 |
| 6,936,719 B2 | 8/2005 | Babu et al. | 546/323 |
| 6,956,037 B2 | 10/2005 | Brown et al. | 514/235.5 |
| 7,125,898 B2 | 10/2006 | Aston et al. | |
| 7,151,118 B2 | 12/2006 | Angell et al. | |
| 7,166,623 B2 | 1/2007 | Angell et al. | |
| 2001/0011135 A1 | 8/2001 | Reidl et al. | |
| 2003/0055088 A1 | 3/2003 | Shao et al. | |
| 2003/0139605 A1 | 7/2003 | Riedl et al. | 546/291 |
| 2003/0225089 A1 | 12/2003 | Jung et al. | 514/242 |
| 2004/0038858 A1 | 2/2004 | Dorsch et al. | |
| 2004/0116479 A1 | 6/2004 | Haviv et al. | |
| 2004/0138287 A1 | 7/2004 | Barth et al. | 514/419 |
| 2004/0162281 A1 | 8/2004 | Babu et al. | 514/217.03 |
| 2004/0176446 A1 | 9/2004 | Alonso-Alija et al. | |
| 2004/0242868 A1 | 12/2004 | Angell et al. | |
| 2004/0249161 A1 | 12/2004 | Angell et al. | |
| 2004/0254200 A1 | 12/2004 | Davis et al. | 514/260.1 |
| 2004/0266839 A1 | 12/2004 | Angell et al. | |
| 2004/0267012 A1 | 12/2004 | Angell et al. | |
| 2005/0020540 A1 | 1/2005 | Angell et al. | |
| 2005/0020590 A1 | 1/2005 | Lang et al. | |
| 2005/0038014 A1 | 2/2005 | Angell et al. | |
| 2005/0065195 A1 | 3/2005 | Angell et al. | |
| 2005/0090491 A1 | 4/2005 | Angell et al. | |
| 2006/0089393 A1 | 4/2006 | Angell et al. | |
| 2006/0122221 A1 | 6/2006 | Angell et al. | |
| 2006/0264479 A1 | 11/2006 | Aston et al. | |
| 2006/0276516 A1 | 12/2006 | Aston et al. | |

FOREIGN PATENT DOCUMENTS

| | | |
|---|---|---|
| EP | 0 533 268 | 9/1992 |
| EP | 0 346 841 | 6/2003 |
| EP | 0 430 033 | 4/2004 |
| GB | 2 276 161 | 3/1993 |
| GB | 2 276 162 | 3/1993 |
| GB | 2 273 930 | 12/1993 |
| GB | 2 295 387 | 5/1996 |
| JP | 11218884 | 8/1999 |
| WO | WO94/15920 | 7/1994 |
| WO | WO95/06636 | 3/1995 |
| WO | WO95/06644 | 3/1995 |
| WO | WO95/11243 | 4/1995 |
| WO | WO95/15954 | 6/1995 |
| WO | WO95/17401 | 6/1995 |
| WO | WO95/29907 | 11/1995 |
| WO | WO95/30675 | 11/1995 |
| WO | WO96/31508 | 10/1996 |
| WO | WO96/31509 | 10/1996 |
| WO | WO97/03034 | 1/1997 |
| WO | WO98/57934 | 12/1998 |
| WO | WO99/32463 | 7/1999 |
| WO | WO 00/12074 | 3/2000 |
| WO | WO 00/12497 | 3/2000 |
| WO | WO 00/26216 | 5/2000 |
| WO | WO 00/56738 | 9/2000 |
| WO | WO 00/71493 | 11/2000 |
| WO | WO 00/71509 | 11/2000 |
| WO | WO 00/71510 | 11/2000 |
| WO | WO 00/71511 | 11/2000 |
| WO | WO 01/27089 | 4/2001 |
| WO | WO 01/34605 | 5/2001 |
| WO | WO 01/70695 | 9/2001 |
| WO | WO 01/87875 | 11/2001 |
| WO | WO 02/40486 | 5/2002 |
| WO | WO 03/032970 | 4/2003 |
| WO | WO 03/068747 | 8/2003 |
| WO | WO 03/093248 | 11/2003 |
| WO | WO 04/010995 | 2/2004 |
| WO | WO 04/089874 | 10/2004 |
| WO | WO 04/089875 | 10/2004 |
| WO | WO 05/014550 | 2/2005 |
| WO | WO 05/061465 | 7/2005 |
| WO | WO 06/110173 | 10/2006 |

OTHER PUBLICATIONS

Hanson, *Expert Opinion on Therapeutic Patents*, vol. 7(7) pp. 729-733 (1997).
Henry et al., *Drugs of the Future*, vol. 24 (12) pp. 1345-1354 (1999).
Jiang et al, *Journal of Biological Chemistry*, vol. 271 (30) pp. 17920-17926 (1996).
Li et al., *Biochemical and Biophysical Research Communications*, vol. 228 (2) pp. 334-340 (1996).
Liebeskind et al., *Organic Letters*, vol. 4 (6) pp. 979-981 (2002).
Moreland et al., *Annals of Internal Medicine*, vol. 130 (6) pp. 478-486 (1999).
Murali Dhar et al., *Bioorganic and Medicinal Chemistry Letters*, vol. 12 (21) pp. 3125-3128 (2002).
Rankin et al., *British Journal of Rheumatology*, vol. 34 pp. 334-342 (1995).
Salituro et al., *Current Medicinal Chemistry*, vol. 6 pp. 807-823 (1999).
Wang et al., *Journal of Biological Chemistry*, vol. 272 (38) pp. 23668-23674 (1997).
U.S. Appl. No. 10/492,714, filed Apr. 15, 2004, Angell et al.
U.S. Appl. No. 10/568,121, filed Feb. 9, 2006, Walker, A.
U.S. Appl. No. 10/551,503, filed Sep. 30, 2005, Aston, N.
U.S. Appl. No. 10/551,502, filed Sep. 30, 2005, Aston et al.
U.S. Appl. No. 10/492,713, filed Apr. 15, 2004, Angell et al.
U.S. Appl. No. 10/587,614, filed Jan. 27, 2005, Campos et al.
U.S. Appl. No. 10/587,613, filed Jan. 27, 2005, Patel et al.
U.S. Appl. No. 10/587,790, filed Jan. 27, 2005, Bamborough et al.
U.S. Appl. No. 10/587,989, filed Jan. 27, 2005, Barker et al.
U.S. Appl. No. 11/557,607, filed Nov. 8, 2006, Angell et al.
U.S. Appl. No. 11/556,285, filed Nov. 3, 2006, Angell et al.
Courtney, S. et al., *Bioorganic & Medicinal Chemistry Letters*, vol. 14 pp. 3269-3273 (2004).
Foster, et al., *Drug News Perspect.*, vol. 13(8) pp. 488-497 (2000).
Henry, J. et al., *Bioorganic & Medicinal Chemistry Letters*, vol. 8 pp. 3335-3340 (1998).
Marin, et al., *Blood*, vol. 98(3) pp. 667-673 (2001).
Herlaar, et al., Molecular Medicine Today, vol. 5 pp. 439-447 (1999).

BIPHENYLCARBOXYLIC AMIDE DERIVATIVES AS P38 KINASE INHIBITORS

This application claims the benefit of §371 application of PCT/EP2004/003773, filed 7 Apr. 2004.

This invention relates to novel compounds and their use as pharmaceuticals, particularly as p38 kinase inhibitors, for the treatment of certain diseases and conditions.

We have now found a group of novel compounds that are inhibitors of p38 kinase.

According to the invention there is provided a compound of formula (I):

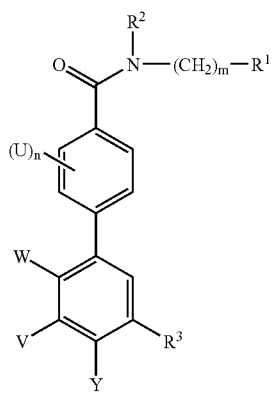

wherein $R^1$ is selected from $C_{1-6}$alkyl substituted by one to three groups independently selected from oxo, cyano and —S(O)$_p$R$^4$, and $C_{3-7}$cycloalkyl optionally substituted by up to three groups independently selected from oxo, cyano, —S(O)$_p$R$^4$, OH, halogen, $C_{1-6}$alkoxy, —NR$^5$R$^6$, —CONR$^5$R$^6$, —NCOR$^5$, —COOR$^5$, —SO$_2$NR$^5$R$^6$, —NHSO$_2$R$^5$ and —NHCONHR$^5$, $R^2$ is selected from hydrogen, $C_{1-6}$alkyl and —(CH$_2$)$_q$—C$_{3-7}$cycloalkyl, or (CH$_2$)$_m$R$^1$ and $R^2$, together with the nitrogen atom to which they are bound, form a four- to six-membered heterocyclic ring optionally containing one or two additional heteroatoms independently selected from oxygen, sulphur and N—R$^7$, wherein the ring is optionally substituted by one or two groups independently selected from oxo, $C_{1-6}$alkyl, halogen and trifluoromethyl;

$R^3$ is the group —CO—NH—(CH$_2$)$_r$—R$^8$ or —NH—CO—R$^9$;

$R^4$ is selected from hydrogen, $C_{1-6}$alkyl, heterocyclyl optionally substituted by $C_{1-4}$alkyl, and phenyl wherein the phenyl is optionally substituted by up to two groups independently selected from $C_{1-6}$alkoxy, $C_{1-6}$alkyl and halogen;

$R^5$ is selected from hydrogen, $C_{1-6}$alkyl and phenyl wherein the phenyl group is optionally substituted by up to two substituents selected from $C_{1-6}$alkyl and halogen, $R^6$ is selected from hydrogen and $C_{1-6}$alkyl, or $R^5$ and $R^6$, together with the nitrogen atom to which they are bound, form a five- to six-membered heterocyclic or heteroaryl ring optionally containing up to one additional heteroatom selected from oxygen, sulfur and nitrogen, wherein the ring is optionally substituted by up to two $C_{1-6}$alkyl groups;

$R^7$ is selected from hydrogen and methyl;

when r is 0 to 2, $R^8$ is selected from hydrogen, $C_{1-6}$alkyl, $C_{3-7}$cycloalkyl, CONHR$^5$, phenyl optionally substituted by $R^{10}$ and/or $R^{11}$, heteroaryl optionally substituted by $R^{10}$ and/or $R^{11}$ and heterocyclyl optionally substituted by $R^{10}$ and/or $R^{11}$, and when r is 2, $R^8$ is additionally selected from $C_{1-6}$alkoxy, NHCOR$^5$, NHCONHR$^5$, NR$^5$R$^6$ and OH;

$R^9$ is selected from hydrogen, $C_{1-6}$alkyl, $C_{1-6}$alkoxy, —(CH$_2$)$_s$—C$_{3-7}$cycloalkyl, trifluoromethyl, —(CH$_2$)$_t$phenyl optionally substituted by $R^{12}$ and/or $R^{13}$, —(CH$_2$)$_t$heteroaryl optionally substituted by $R^{12}$ and/or $R^{13}$, —(CH$_2$)$_t$heterocyclyl optionally substituted by $R^{12}$ and/or $R^{13}$ and —(CH$_2$)$_t$ fused bicyclyl optionally substituted by $R^{12}$ and/or $R^{13}$;

$R^{10}$ is selected from $C_{1-6}$alkyl, $C_{1-6}$alkoxy, —CONR$^6$R$^{14}$, —NHCOR$^{14}$, —SO$_2$NHR$^{14}$, —NHSO$_2$R$^{14}$, halogen, trifluoromethyl, —X—(CH$_2$)$_j$-phenyl optionally substituted by one or more halogen atoms or $C_{1-6}$alkyl groups, —X—(CH$_2$)$_j$-heterocyclyl or —X—(CH$_2$)$_j$-heteroaryl wherein the heterocyclyl or heteroaryl group is optionally substituted by one or more substituents selected from $C_{1-6}$alkyl, $R^{11}$ is selected from $C_{1-6}$alkyl and halogen, or when $R^{10}$ and $R^{11}$ are ortho substituents, then together with the carbon atoms to which they are bound, $R^{10}$ and $R^{11}$ may form a five- or six-membered saturated or unsaturated ring to give a fused bicyclic ring system, wherein the ring that is formed by $R^{10}$ and $R^{11}$ optionally contains one or two heteroatoms selected from oxygen, nitrogen and sulfur;

$R^{12}$ is selected from $C_{1-6}$alkyl, $C_{1-6}$alkoxy, —(CH$_2$)$_s$—C$_{3-7}$cycloalkyl, —CONR$^{15}$R$^{16}$, —NHCOR$^{16}$, —SO$_2$NHR$^{15}$, —NHSO$_2$R$^{16}$, halogen, —(CH$_2$)$_k$NR$^{17}$R$^{18}$, oxy, trifluoromethyl, phenyl optionally substituted by one or more $R^{13}$ groups and heteroaryl wherein the heteroaryl is optionally substituted by one or more $R^{13}$ groups, $R^{13}$ is selected from $C_{1-6}$alkyl, $C_{1-6}$alkoxy, halogen, trifluoromethyl and —NR$^{17}$R$^{18}$, or $R^{12}$ and $R^{13}$, together with the carbon atoms to which they are bound, form a five- or six-membered saturated or unsaturated ring to give a fused bicyclic ring system, wherein the ring that is formed by $R^{12}$ and $R^{13}$ optionally contains one or two heteroatoms selected from oxygen, nitrogen and sulfur;

$R^{14}$ is selected from hydrogen and $C_{1-6}$alkyl;

$R^{15}$ is selected from hydrogen, $C_{1-6}$alkyl and phenyl wherein the phenyl group may be optionally substituted by one or more $R^{13}$ groups, $R^{16}$ is selected from hydrogen and $C_{1-6}$alkyl, or $R^{15}$ and $R^{16}$, together with the nitrogen atom to which they are bound, form a five- to six-membered heterocyclic ring optionally containing one additional heteroatom selected from oxygen, sulfur and N—R$^7$, wherein the ring is optionally substituted by up to two $C_{1-6}$alkyl groups;

$R^{17}$ is selected from hydrogen, $C_{1-6}$alkyl and —(CH$_2$)$_s$—C$_{3-7}$cycloalkyl optionally substituted by $C_{1-6}$alkyl, $R^{18}$ is selected from hydrogen and $C_{1-6}$alkyl, or $R^{17}$ and $R^{18}$, together with the nitrogen atom to which they are bound, form a three- to seven-membered heterocyclic ring optionally containing one additional heteroatom selected from oxygen, sulfur and N—R$^7$, wherein the ring may contain up to one double bond and the ring is optionally substituted by one or more $R^{19}$ groups;

$R^{19}$ is selected from $C_{1-6}$alkyl, oxy, —CH$_2$OC$_{1-6}$alkyl, trichloromethyl and —N(C$_{1-6}$alkyl)$_2$;

X is selected from —O— and a bond;

U is selected from methyl and halogen;

W is selected from methyl and chlorine;

V and Y are each selected Independently from hydrogen, methyl and halogen;

m is selected from 0, 1, 2, 3 and 4 wherein each carbon atom of the resulting carbon chain is optionally substituted with one or two groups selected independently from $C_{1-6}$alkyl, wherein the $C_{1-6}$alkyl group is optionally substituted by up to three OH groups;

n, p, r and j are independently selected from 0, 1 and 2;

q and k are independently selected from 0, 1, 2 and 3; and s and t are independently selected from 0 and 1;

with the proviso that when $R^1$ is unsubstituted $C_{3-7}$cycloalkyl, m is not selected from 0, 1, 2, 3 and 4 wherein each carbon atom of the resulting carbon chain may be optionally substituted with one or two groups selected independently from $C_{1-6}$alkyl;

or a pharmaceutically acceptable derivative thereof.

In a preferred embodiment, the molecular weight of a compound of formula (I) does not exceed 1000, more preferably 800, even more preferably 600.

In one embodiment, $R^1$ is selected from $C_{2-6}$alkyl, for example ethyl, 2-butyl, isobutyl or 2-methylpent-2-yl, substituted by one or two groups, preferably one group, independently selected from oxo, cyano and —S(O)$_p$R$^4$; and $C_{3-6}$cycloalkyl optionally substituted by one or two groups, preferably one group, independently selected from OH and cyano. Representative examples of $R^1$ include $C_{4-6}$alkyl substituted by oxo, in particular —C(O)CH(CH$_3$)$_2$ and —C(CH$_3$)$_2$CH$_2$C(O)CH$_3$; $C_{2-4}$alkyl substituted by cyano, in particular —CH$_2$CH$_2$CN and —C(CH$_3$)(CH$_2$CH$_3$)CN; $C_{2-4}$alkyl substituted by —S(O)$_p$R$^4$, in particular —CH$_2$CH$_2$SCH$_3$ and —CH$_2$CH$_2$SO$_2$CH$_3$; and $C_{3-6}$cycloalkyl optionally substituted by OH or cyano, in particular cyclopropyl, 1-hydroxycyclohexyl and 1-cyanocyclohexyl.

In one embodiment, $R^2$ is selected from hydrogen, $C_{1-4}$alkyl and —CH$_2$-cyclopropyl. A representative example of $R^2$ is hydrogen.

Alternatively, in another embodiment, (CH$_2$)$_m$R$^1$ and R$^2$, together with the nitrogen atom to which they are bound, form a four- to six-membered heterocyclic ring optionally containing one or two additional heteroatoms independently selected from oxygen, sulphur and N—R$^7$. Representative examples include an azetidinyl or pyrrolidinyl ring.

A representative example of $R^3$ is —CO—NH—(CH$_2$)$_r$R$^8$.

In one embodiment, $R^4$ is selected from hydrogen, $C_{1-4}$alkyl and phenyl. A representative example of $R^4$ is $C_{1-4}$alkyl, in particular methyl.

In one embodiment, $R^5$ is selected from hydrogen, $C_{1-4}$alkyl and phenyl optionally substituted by up to two substitutents selected from methyl and halogen.

In one embodiment, $R^6$ is selected from hydrogen and $C_{1-4}$alkyl.

In one embodiment, $R^8$ is selected from $C_{1-4}$alkyl, in particular methyl, ethyl or n-propyl; $C_{3-6}$cycloalkyl, in particular cyclopropyl or cyclobutyl; CONHR$^5$; phenyl optionally substituted by R$^{10}$ and/or R$^{11}$; and heteroaryl, in particular thiazolyl, pyrazolyl, thiadiazolyl or pyridyl, optionally substituted by R$^{10}$ and/or R$^{11}$. A representative example of $R^8$ is $C_{3-6}$cycloalkyl, in particular cyclopropyl.

In one embodiment, $R^9$ is selected from $C_{1-4}$alkyl, in particular methyl, ethyl, n-propyl or isobutyl; —(CH$_2$)$_s$—$C_{3-6}$cycloalkyl, in particular cyclopropyl, —CH$_2$-cyclopropyl, cyclobutyl or cyclopentyl; trifluoromethyl; —(CH$_2$)$_t$phenyl optionally substituted by R$^{12}$ and/or R$^{13}$; —(CH$_2$)$_t$heteroaryl optionally substituted by R$^{12}$ and/or R$^{13}$, in particular furyl, —CH$_2$-furyl, thienyl, thiazolyl, isoxazolyl, pyrazolyl, pyridyl, pyrimidinyl or pyrazinyl optionally substituted by R$^{12}$ and/or R$^{13}$; —(CH$_2$)$_t$heterocyclyl optionally substituted by R$^{12}$ and/or R$^{13}$ in particular tetrahydrofuranyl and tetrahydropyranyl; and —(CH$_2$)$_t$fused bicyclyl optionally substituted by R$^{12}$ and/or R$^{13}$ in particular quinolyl.

In one embodiment, $R^{10}$ is selected from $C_{1-4}$alkyl, in particular t-butyl; —CONR$^6$R$^{14}$, in particular —CONH$_2$; —NHCOR$^{14}$, in particular —NHCOCH$_3$; —X—(CH$_2$)$_j$-phenyl optionally substituted by chlorine or methyl; and —X—(CH$_2$)$_j$-heterocyclyl or —X—(CH$_2$)$_j$-heteroaryl, in particular pyrrolinyl, pyrrolidinyl, piperidinyl, morpholino, thiomorpholino, pyridinyl, pyrimidinyl or oxadiazolyl, wherein the heterocyclyl or heteroaryl group may be optionally substituted by one or more substituents selected from $C_{1-6}$alkyl.

In one embodiment, $R^{11}$ is halogen.

In one embodiment, $R^{12}$ is selected from $C_{1-4}$alkyl, in particular methyl or ethyl; $C_{1-4}$alkoxy, in particular methoxy; —(CH$_2$)$_s$—$C_{3-6}$cycloalkyl, in particular cyclopropyl or cyclohexyl; halogen, in particular chlorine; —(CH$_2$)$_k$—NR$^{17}$R$^{18}$; phenyl optionally substituted by one or more R$^{13}$ groups; and heteroaryl, in particular furyl, thienyl, pyrrolyl or pyridyl, wherein the heteroaryl may be optionally substituted by one or more R$^{13}$ groups.

In one embodiment, $R^{13}$ is selected from $C_{1-2}$alkyl, in particular methyl; halogen, in particular fluorine or chlorine; trifluoromethyl and —NR$^{17}$R$^{18}$.

In one embodiment, $R^{14}$ is $C_{1-4}$alkyl.

In one embodiment, $R^{15}$ is selected from hydrogen and $C_{1-4}$alkyl.

In one embodiment, $R^{16}$ is selected from hydrogen and $C_{1-4}$alkyl.

In one embodiment, $R^{17}$ is selected from hydrogen; $C_{1-4}$alkyl, in particular methyl, ethyl or isobutyl; and —(CH$_2$)$_s$—$C_{3-6}$cycloalkyl in particular cyclopropyl, —CH$_2$-cyclopropyl, cyclobutyl or cyclohexyl.

In one embodiment, $R^{18}$ is selected from hydrogen and $C_{1-4}$alkyl.

In another embodiment, $R^{17}$ and $R^{18}$, together with the nitrogen atom to which they are bound, form a five- to six-membered heterocyclic ring optionally containing one additional heteroatom selected from oxygen, sulfur and N—R$^7$, and the ring is optionally substituted by one or more R$^{19}$ groups.

In one embodiment, $R^{19}$ is selected from $C_{1-4}$alkyl, in particular methyl; oxy; —CH$_2$OC$_{1-4}$alkyl, in particular —CH$_2$OCH$_3$; and —N(C$_{1-6}$alkyl)$_2$, in particular —N(CH$_3$)$_2$.

In one embodiment, X is a bond.

In one embodiment, U is methyl or fluorine.

A representative example of W is methyl.

In one embodiment, V and Y are each selected independently from hydrogen, chlorine and fluorine. A representative example of V is fluorine. A representative example of Y is hydrogen.

In one embodiment, when $R^1$ is unsubstituted $C_{3-7}$cycloalkyl, m is selected from 1, 2, 3 and 4 wherein at least one carbon atom of the resulting carbon chain is substituted with one or two groups selected independently from $C_{1-6}$alkyl, wherein the $C_{1-6}$alkyl is substituted by one to three OH groups. In another embodiment, m is selected from 0, 1 and 2, and when the carbon chain of m is substituted, these substituents are preferably one or two methyl groups optionally substituted by one or two OH groups. Representative examples of m include 0 and 1 wherein the carbon chain is optionally substituted by one or two methyl groups which are optionally substituted by OH.

In one embodiment, n is selected from 0 and 1. A representative example of n is 0.

Representative examples of p are 0 and 2.

In one embodiment, r is selected from 0 and 1. A representative example of r is 0.

In one embodiment, s is 0.

In one embodiment, t is 0.

In one embodiment, j is selected from 0 and 1.

In one embodiment, k is selected from 0, 1 and 2.

It is to be understood that the present invention covers all combinations of particular and preferred groups described hereinabove.

Particular compounds according to the invention include those mentioned in the examples and their pharmaceutically acceptable derivatives.

As used herein, the term "pharmaceutically acceptable" means a compound which is suitable for pharmaceutical use. Salts and solvates of compounds of the invention which are suitable for use in medicine are those wherein the counterion or associated solvent is pharmaceutically acceptable. However, salts and solvates having non-pharmaceutically acceptable counterions or associated solvents are within the scope of the present invention, for example, for use as intermediates in the preparation of other compounds of the invention and their pharmaceutically acceptable salts and solvates.

As used herein, the term "pharmaceutically acceptable derivative", means any pharmaceutically acceptable salt, solvate, or prodrug e.g. ester, of a compound of the invention, which upon administration to the recipient is capable of providing (directly or indirectly) a compound of the invention, or an active metabolite or residue thereof. Such derivatives are recognizable to those skilled in the art, without undue experimentation. Nevertheless, reference is made to the teaching of Burger's Medicinal Chemistry and Drug Discovery, 5$^{th}$ Edition, Vol 1: Principles and Practice, which is incorporated herein by reference to the extent of teaching such derivatives. Preferred pharmaceutically acceptable derivatives are salts, solvates, esters, carbamates and phosphate esters. Particularly preferred pharmaceutically acceptable derivatives are salts, solvates and esters. Most preferred pharmaceutically acceptable derivatives are salts and esters.

The compounds of the present invention may be in the form of and/or may be administered as a pharmaceutically acceptable salt. For a review on suitable salts see Berge et al., J. Pharm. Sci., 1977, 66, 1-19.

Typically, a pharmaceutical acceptable salt may be readily prepared by using a desired acid or base as appropriate. The salt may precipitate from solution and be collected by filtration or may be recovered by evaporation of the solvent.

Salts of the compounds of the present invention may, for example, comprise acid addition salts resulting from reaction of an acid with a nitrogen atom present in a compound of formula (I). Salts encompassed within the term "pharmaceutically acceptable salts" refer to non-toxic salts of the compounds of this invention. Suitable addition salts are formed from acids which form non-toxic salts and examples are acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, ethanesulphonate, formate, fumarate, gluceptate, gluconate, glutamate, glycollylarsanilate, hexylresorcinate, hydrabamine, hydrobromide, hydrochloride, hydrogen phosphate, hydroiodide, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, oxaloacetate, pamoate (embonate), palmitate, pantothenate, phosphate/diphosphate, piruvate, polygalacturonate, saccharate, salicylate, stearate, subacetate, succinate, sulphate, tannate, tartrate, teoclate, tosylate, triethiodide, trifluoroacetate and valerate.

Pharmaceutically acceptable base salts include ammonium salts such as a trimethylammonium salt, alkali metal salts such as those of sodium and potassium, alkaline earth metal salts such as those of calcium and magnesium and salts with organic bases, including salts of primary, secondary and tertiary amines, such as isopropylamine, diethylamine, ethanolamine, trimethylamine, dicyclohexyl amine and N-methyl-D-glucamine.

Those skilled in the art of organic chemistry will appreciate that many organic compounds can form complexes with solvents in which they are reacted or from which they are precipitated or crystallized. These complexes are known as "solvates". As used herein, the term "solvate" refers to a complex of variable stoichiometry formed by a solute (in this invention, a compound of formula (I) or a salt thereof) and a solvent. Such solvents for the purpose of the invention may not interfere with the biological activity of the solute. Examples of suitable solvents include water, methanol, ethanol and acetic acid. Preferably the solvent used is a pharmaceutically acceptable solvent. Examples of suitable pharmaceutically acceptable solvents include water, ethanol and acetic acid. Most preferably the solvent used is water. A complex with water is known as a "hydrate". Solvates of the compound of the invention are within the scope of the invention.

As used herein, the term "prodrug" means a compound which is converted within the body, e.g. by hydrolysis in the blood, into its active form that has medical effects. Pharmaceutically acceptable prodrugs are described in T. Higuchi and V. Stella, Prodrugs as Novel Delivery Systems, Vol. 14 of the A.C.S. Symposium Series; Edward B. Roche, ed., Bioreversible Carriers in Drug Design, American Pharmaceutical Association and Pergamon Press, 1987; and in D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

Prodrugs are any covalently bonded carriers that release a compound of formula (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol, sulfhydryl and amine functional groups of the compounds of formula (I). Further, in the case of a carboxylic acid (—COOH), esters may be employed, such as methyl esters, ethyl esters, and the like. Esters may be active in their own right and/or be hydrolysable under in vivo conditions in the human body. Suitable pharmaceutically acceptable in vivo hydrolysable ester groups include those which break down readily in the human body to leave the parent acid or its salt.

As used herein, the term "alkyl" refers to straight or branched hydrocarbon chains containing the specified number of carbon atoms. For example, $C_{1-6}$alkyl means a straight or branched alkyl containing at least 1, and at most 6, carbon atoms. Examples of "alkyl" as used herein include, but are not limited to, methyl, ethyl, n-propyl, n-butyl, n-pentyl, isobutyl, isopropyl, t-butyl and hexyl. A $C_{1-4}$alkyl group is preferred, for example methyl, ethyl, isopropyl or t-butyl. The said alkyl groups may be optionally substituted with one or more fluorine atoms for example, trifluoromethyl.

As used herein, the term "alkoxy" refers to straight or branched chain alkoxy groups containing the specified number of carbon atoms. For example, $C_{1-6}$alkoxy means a straight or branched alkoxy containing at least 1, and at most 6, carbon atoms. Examples of "alkoxy" as used herein include, but are not limited to, methoxy, ethoxy, propoxy, prop-2-oxy, butoxy, but-2-oxy, 2-methylprop-1-oxy, 2-methylprop-2-oxy, pentoxy and hexyloxy. A $C_{1-4}$alkoxy group is preferred, for example methoxy or ethoxy.

As used herein, the term "cycloalkyl" refers to a non-aromatic hydrocarbon ring containing the specified number of carbon atoms which may optionally contain up to one double bond. For example, $C_{3-7}$cycloalkyl means a non-aromatic ring containing at least three, and at most seven, ring carbon atoms. Examples of "cycloalkyl" as used herein include, but are not limited to, cyclopropyl, cyclobutyl, cyclopentyl, cyclohexyl and cycloheptyl. A $C_{3-6}$cycloalkyl group is preferred, for example, cyclopropyl, cyclopentyl or cyclohexyl. When $R^1$ is a $C_{3-7}$cycloalkyl group, the cycloalkyl group may be optionally substituted by one or more groups selected from $C_{1-6}$alkyl and phenyl.

As used herein, the terms "heteroaryl ring" and "heteroaryl" refer to a monocyclic five- to seven-membered unsaturated hydrocarbon ring containing at least one heteroatom independently selected from oxygen, nitrogen and sulfur. Preferably, the heteroaryl ring has five or six ring atoms. Examples of heteroaryl rings include, but are not limited to, furyl, thienyl, pyrrolyl, oxazolyl, thiazolyl, isoxazolyl, isothiazolyl, imidazolyl, pyrazolyl, oxadiazolyl, triazolyl, tetrazolyl, thiadiazolyl, pyridyl, pyridazinyl, pyrimidinyl, pyrazinyl and triazinyl. The said ring may be optionally substituted by one or more substituents independently selected from $C_{1-6}$alkyl and oxy.

As used herein, the terms "heterocyclic ring" or "heterocyclyl" refer to a monocyclic three- to seven-membered saturated or non-aromatic, unsaturated hydrocarbon ring containing at least one heteroatom independently selected from oxygen, nitrogen and sulfur. Preferably, the heterocyclyl ring has five or six ring atoms. Examples of heterocyclyl groups include, but are not limited to, aziridinyl, pyrrolinyl, pyrrolidinyl, imidazolinyl, imidazolidinyl, pyrazolinyl, pyrazolidinyl, piperidyl, piperazinyl, morpholino, tetrahydropyranyl, tetrahydrofuranyl and thiomorpholino. The said ring may be optionally substituted by one or more substituents independently selected from $C_{1-6}$alkyl and oxy.

As used herein, the term "fused bicyclic ring system" refers to a ring system comprising two five- to seven-membered saturated or unsaturated rings, the ring system optionally containing one or more heteroatoms independently selected from oxygen, nitrogen and sulfur. Preferably, each ring has five or six ring atoms. Examples of suitable fused bicyclic rings include, but are not limited to, naphthyl, indolyl, isoindolyl, azaindolyl, indolinyl, benzothienyl, benzoxazolyl, benzimidazolyl, benzothiazolyl, benzofuranyl, quinolyl, isoquinolyl, quinazolinyl, cinnolinyl, phthalazinyl, tetrahydroquinolyl, benzodioxanyl, indanyl and tetrahydronaphthyl. Each ring may be optionally substituted with one or more substituents independently selected from halogen, $C_{1-6}$alkyl, oxy, $-(CH_2)_k NR^{17}R^{18}$, $-CO(CH_2)_k NR^{17}R^{18}$, and imidazolyl. Particularly preferred substituents are chlorine, imidazolyl and $-CH_2-N(CH_3)_2$.

As used herein, the terms "halogen" or "halo" refer to the elements fluorine, chlorine, bromine and iodine. Preferred halogens are fluorine, chlorine and bromine. A particularly preferred halogen is fluorine or chlorine.

As used herein, the term "optionally" means that the subsequently described event(s) may or may not occur, and includes both event(s) which occur and events that do not occur.

As used herein, the term "substituted" refers to substitution with the named substituent or substituents, multiple degrees of substitution being allowed unless otherwise stated.

With regard to stereoisomers, the compounds of structure (I) may have one or more asymmetric carbon atom and may occur as racemates, racemic mixtures and as individual enantiomers or diastereomers. All such isomeric forms are included within the present invention, including mixtures thereof.

Cis (E) and trans (Z) isomerism may also occur. The present invention includes the indivisual stereoisomers of the compound of the invention and, where appropriate, the individual tautomeric forms thereof, together with mixtures thereof.

Separation of diastereoisomers or cis and trans isomers may be achieved by conventional techniques, e.g. by fractional crystallisation, chromatography or H.P.L.C. A stereoisomeric mixture of the agent may also be prepared from a corresponding optically pure intermediate or by resolution, such as H.P.L.C. of the corresponding racemate using a suitable chiral support or by fractional crystallisation of the diastereolsomeric salts formed by reaction of the corresponding racemate with a suitable optically active acid or base, as appropriate.

Furthermore, some of the crystalline forms of the compounds of structure (I) may exist as polymorphs, which are included in the present invention.

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the working Examples.

For example, a general method (A) for preparing the compounds of Formula (I) comprises the reactions set out in Scheme 1 below.

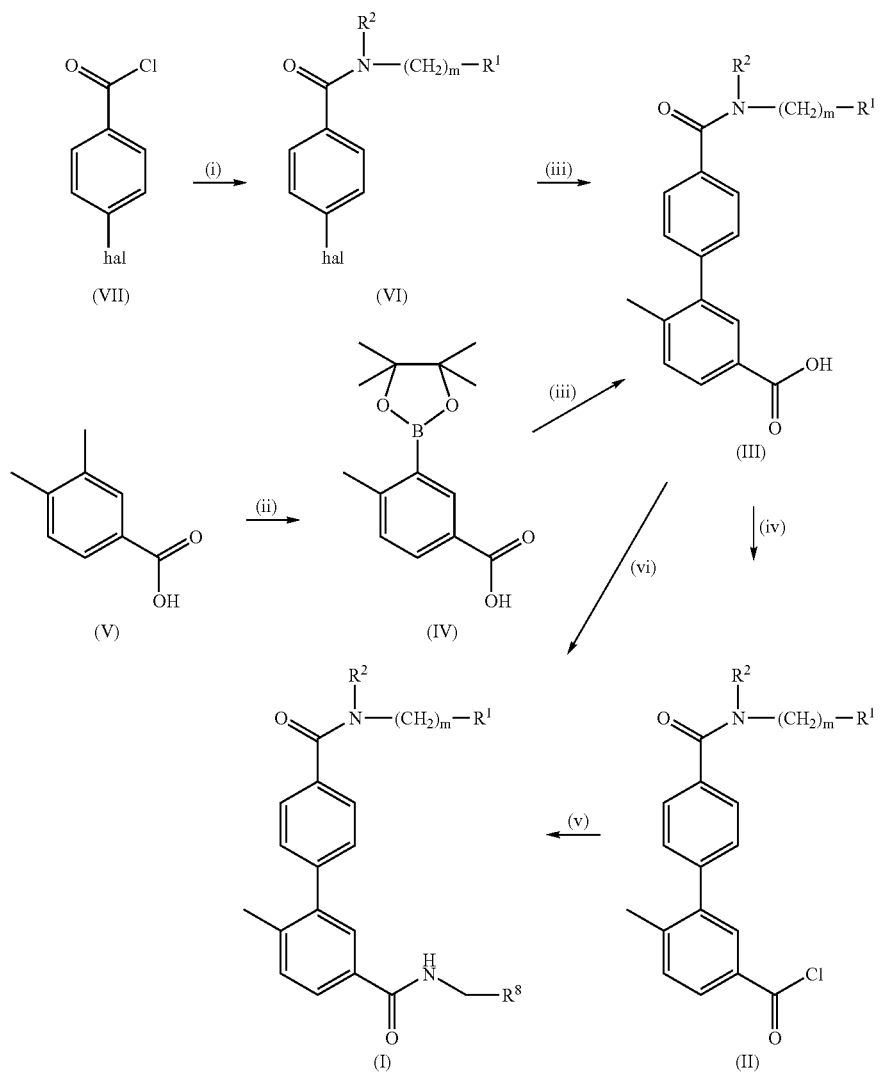
(i) $R^1(CH_2)_mNR^2H$, $Et_3N$, THF
(ii) Bis(pinnacolato)diboron, $PdCl_2dppf$, KOAc, DMF
(iii) $(Ph_3P)_4Pd$, $Na_2CO_3$, DME
(iv) $(COCl)_2$, DMF
(v) $R^8NH_2$, pyridine
(vi) $R^8NH_2$, PyBOP, HOBT, DIPEA, DMF
For example, a general method (B) for preparing the compounds of Formula (I) comprises the reactions set out in Scheme 2 below.
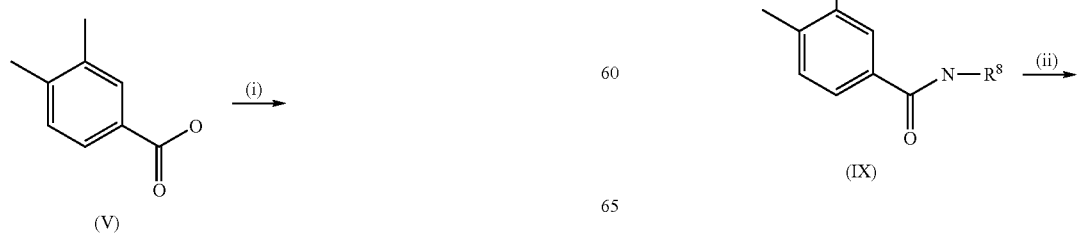

-continued
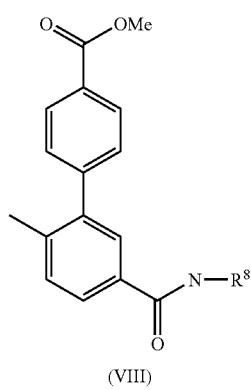
(VIII)
↓ (iii)/(iv)
-continued
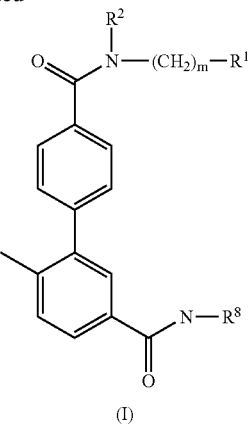
(I)
(i) R⁸NH₂, HATU, HOBT, DIPEA, DMF
(ii) (4-Methoxycarbonylphenyl)boronic acid, (Ph₃P)₄Pd, Na₂CO₃, DME
(iii) NaOH, MeOH, H₂O
(iv) R¹(CH₂)ₘNR²H, HATU, HOBT, DIPEA, THF
For example, a general method (C) for preparing the compounds of Formula (I) comprises the reactions set out in Scheme 3 below.
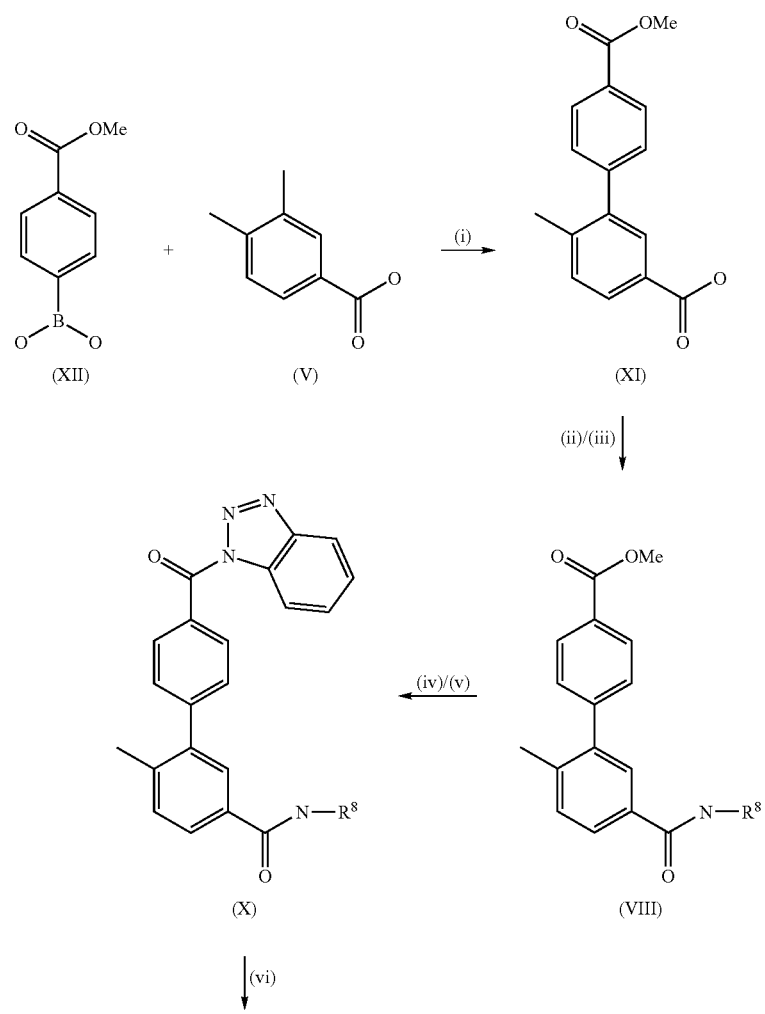

-continued
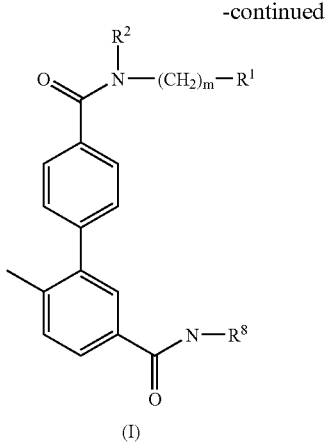
(I)
(i) CsCO$_3$, (PH$_3$P)$_4$Pd, DME
(ii) (COCl)$_2$, CHCl$_3$
(iii) R$^8$NH$_2$
(iv) NaOH, MeOH, H$_2$O
(v) 1-methylsulphonylbenzotriazole, Et$_3$N, THF, DMF
(vi) R$^1$(CH$_2$)$_m$NR$^2$H, THF
For example, a general method (D) for preparing the compounds of Formula (I) comprises the reactions set out in Scheme 4 below.
Scheme 4
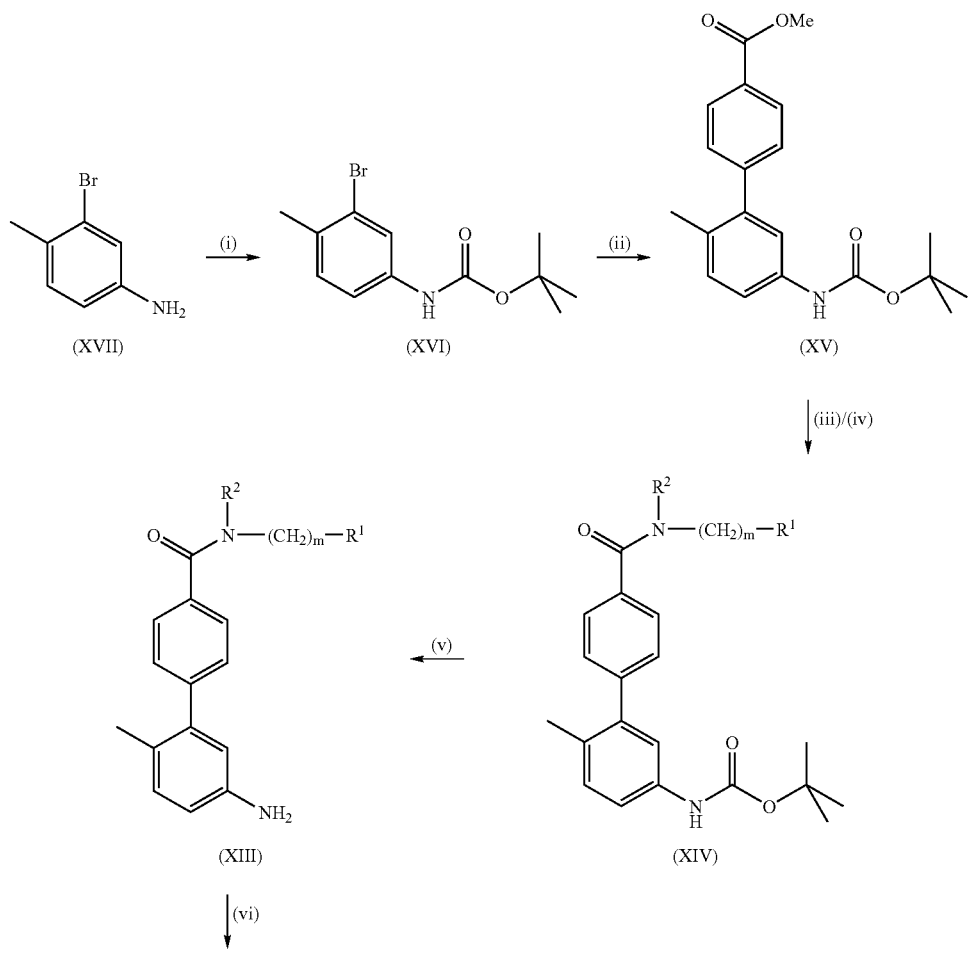

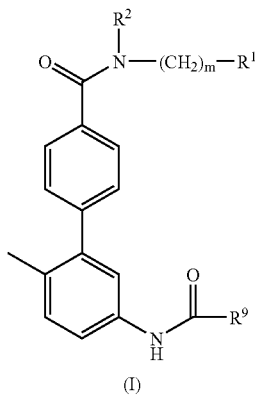

(i) Di-t-butyldicarbonate, Et₃N, DCM
(ii) (4-Methoxycarbonylphenyl)boronic acid, (Ph₃P)₄Pd, CsCO₃, DME
(iii) LiOH, THF, H₂O
(iv) R¹(CH₂)ₘNR²H, HATU, DIPEA, THF
(v) TFA, DCM
(vi) R⁹COOH, HATU, DIPEA, DMF For example, a general method (E) for preparing the compounds of Formula (I) comprises the reactions set out in Scheme 5 below.

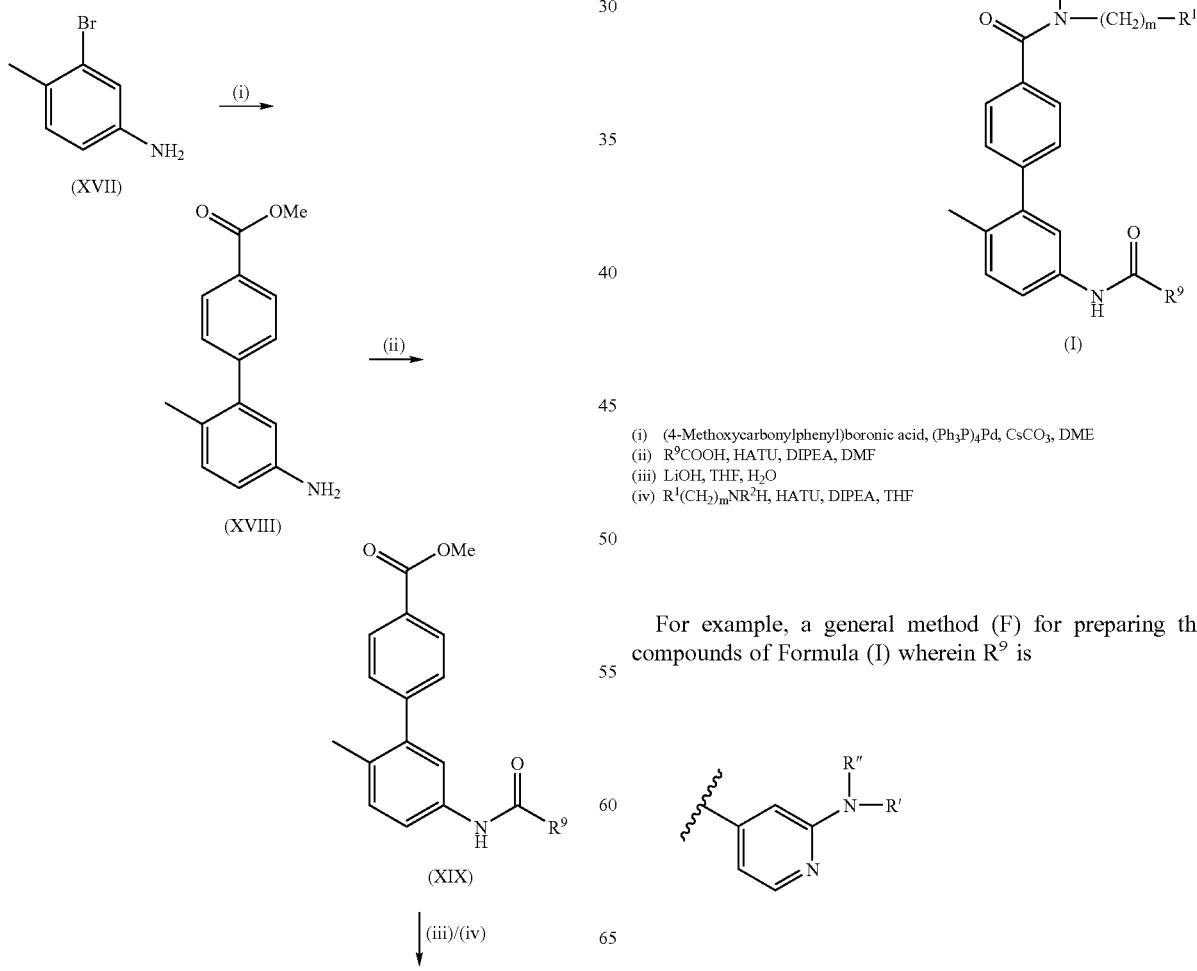

(i) (4-Methoxycarbonylphenyl)boronic acid, (Ph₃P)₄Pd, CsCO₃, DME
(ii) R⁹COOH, HATU, DIPEA, DMF
(iii) LiOH, THF, H₂O
(iv) R¹(CH₂)ₘNR²H, HATU, DIPEA, THF For example, a general method (F) for preparing the compounds of Formula (I) wherein $R^9$ is comprises the reactions set out in Scheme 6 below.

Scheme 6
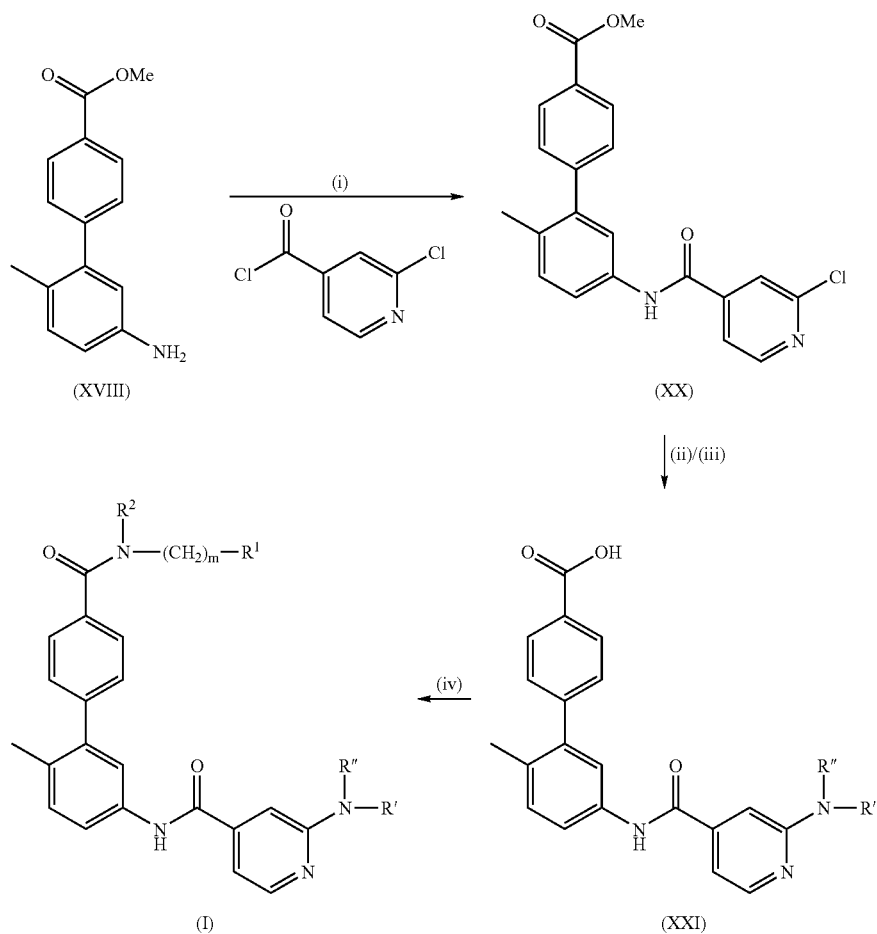
(i) Et$_3$N, DCM
(ii) LiOH, THF, H$_2$O
(iii) R'R"NH
(iv) R$^1$(CH$_2$)$_m$NR$^2$H, HATU, DIPEA, THF
For example, a general method (G) for preparing the compounds of Formula (I) comprises the reactions set out in Scheme 7 below.
Scheme 7
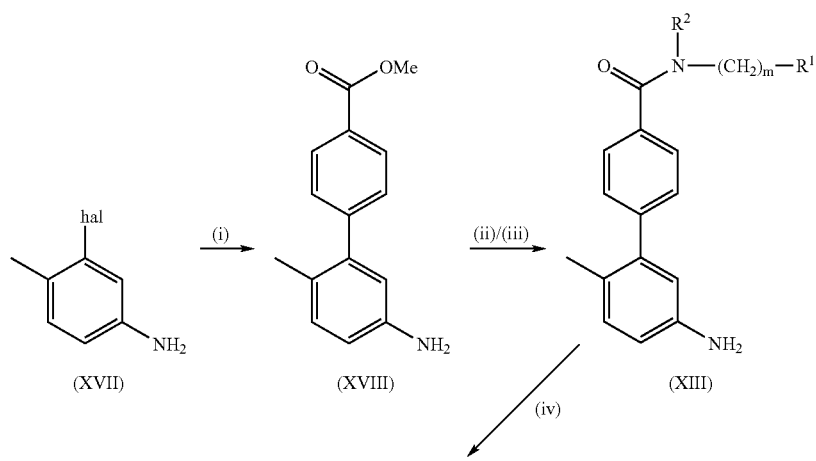

-continued

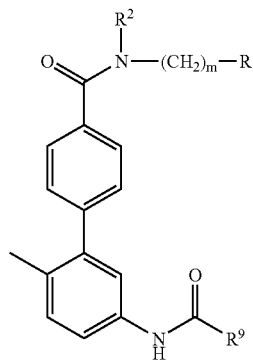
(I)

(i) (4-Methoxycarbonylphenyl)boronic acid, (Ph₃P)₄Pd, CsCO₃, DME
(ii) LiOH, THF, H₂O
(iii) R¹(CH₂)ₘNR²H, HATU, DIPEA, THF
(iv) R⁹COCl, Et₃N, DCM Thus, according to the invention there is provided a process for preparing a compound of formula (I) which comprises:

(a) reacting a compound of formula (XXII)

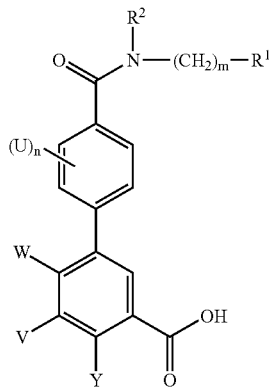
(XXII)

wherein $R^1$, $R^2$, U, W, V, Y, m and n are as defined above, with a compound of formula (XXIII)

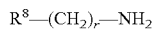
$R^8$—(CH$_2$)$_r$—NH$_2$ (XXIII)

wherein $R^8$ and r are as defined above, under amide forming conditions (if desired, the acid compound (XXII) may be converted to an activated form of the acid, for example the acid chloride, by treatment with, for example, oxalyl chloride, and then the activated acid thus formed reacted with the amine compound (XXIII));

(b) reacting a compound of formula (XXIV)

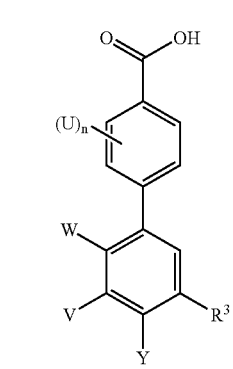
(XXIV)

wherein $R^3$, U, W, V, Y and n are as defined above, with a compound of formula (XXV)

$R^1(CH_2)_mNR^2H$ wherein $R^1$, $R^2$, m and n are as defined above, under amide forming conditions;

(c) reacting a compound of formula (XXVI)

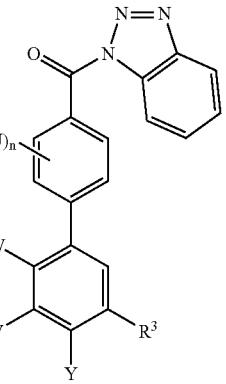
(XXVI)

wherein $R^3$, U, W, V, Y and n are as defined above, with a compound of formula (XXV) as defined above;

(d) reacting a compound of formula (XXVII)

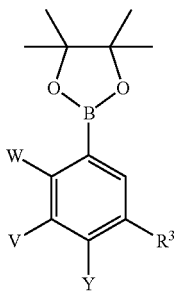

(XXVII)

wherein W, V, Y and $R^3$ are as defined above,
with a compound of formula (XXVIII)

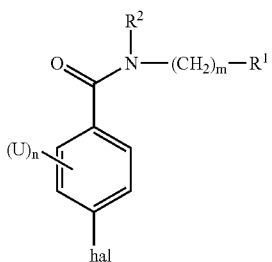

(XXVIII)

wherein $R^1$, $R^2$, U, m and n are as defined above and hal is halogen, in particular bromine or iodine,
in the presence of a catalyst, for example tetrakis(triphenylphosphine)palladium, or
(e) reacting a compound of formula (XXIX)

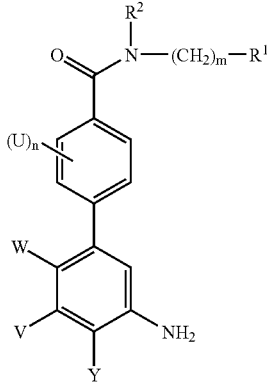

(XXIX)

wherein $R^1$, $R^2$, U, W, V, Y, m and n are as defined above, with a compound of formula (XXX)

$R^9CO_2H$ (XXX)

wherein $R^9$ is as defined above,
under amide forming conditions (if desired, the acid compound (XXX) may be converted to an activated form of the acid, for example the acid chloride, and then the activated acid thus formed reacted with the amine compound (XXIX)).

Suitable amide forming conditions are well known in the art and include treating a solution of the acid, in for example THF, with an amine in the presence of, for example, HOBT, HATU and DIPEA.

Those skilled in the art will appreciate that in the preparation of the compound of the invention or a solvate thereof it may be necessary and/or desirable to protect one or more sensitive groups in the molecule to prevent undesirable side reactions. Suitable protecting groups for use according to the present invention are well known to those skilled in the art and may be used in a conventional manner. See, for example, "Protective groups in organic synthesis" by T. W. Greene and P. G. M. Wuts (John Wiley & sons 1991) or "Protecting Groups" by P. J. Kocienski (Georg Thieme Verlag 1994). Examples of suitable amino protecting groups include acyl type protecting groups (e.g. formyl, trifluoroacetyl, acetyl), aromatic urethane type protecting groups (e.g. benzyloxycarbonyl (Cbz) and substituted Cbz), aliphatic urethane protecting groups (e.g. 9-fluorenylmethoxycarbonyl (Fmoc), t-butyloxycarbonyl (Boc), isopropyloxycarbonyl, cyclohexyloxycarbonyl) and alkyl type protecting groups (e.g. benzyl, trityl, chlorotrityl). Examples of suitable oxygen protecting groups may include for example alky silyl groups, such as trimethylsilyl or tert-butyldimethylsilyl; alkyl ethers such as tetrahydropyranyl or tert-butyl; or esters such as acetate.

Whilst it is possible for the compounds of the present invention to be administered as the raw chemical, the compounds of formula (I) and their pharmaceutically acceptable derivatives are conveniently administered in the form of pharmaceutical compositions eg when the agent is in admixture with a suitable pharmaceutical excipient, diluent and/or carrier selected with regard to the intended route of administration and standard pharmaceutical practice.

Thus, in another aspect of the invention, we provide a pharmaceutical composition comprising at least one compound of formula (I) or a pharmaceutically acceptable derivative thereof, in association with one or more pharmaceutically acceptable excipients, diluents and/or carriers. The excipient, diluent or carrier must be "acceptable" in the sense of being compatible with the other ingredients of the formulation and not deletrious to the receipient thereof.

According to a further aspect, the invention provides a pharmaceutical composition comprising, as active ingredient, at least one compound of the invention or a pharmaceutically acceptable derivative thereof, in association one or more pharmaceutically acceptable excipients, diluents and/or carriers for use in therapy, and in particular in the treatment of human or animal subjects suffering from a condition susceptible to amelioration by an inhibitor of p38 kinase.

The present invention also provides a pharmaceutical composition comprising a therapeutically effective amount of the compounds of the present invention and a pharmaceutically acceptable excipient, diluent and/or carrier (including combinations thereof).

There is further provided by the present invention a process of preparing a pharmaceutical composition, which process comprises mixing at least one compound of the invention or a pharmaceutically acceptable derivative thereof, together with a pharmaceutically acceptable excipient, diluent and/or carrier.

The pharmaceutical compositions may be for human or animal usage in human and veterinary medicine and will typically comprise any one or more of a pharmaceutically acceptable excipient, diluent or carrier. Acceptable carriers or diluents for therapetic use are well known in the pharmaceutical art, and are described, for example, in Remington's Pharmaceutical Sciences, Mack Publishing Co. (A. R. Gennaro edit. 1985). The choice of pharmaceutical excipient, diluent or carrier can be selected with regard to the intended route of administration and standard pharmaceutical practice. The pharmaceutical compositions may comprise as—or in addition to—the excipient, diluent or carrier any suitable binder(s), lubricant(s), suspending agent(s), coating agent(s) and solubilising agent(s).

Preservatives, stabilisers, dyes and even flavouring agents may be provided in the pharmaceutical composition. Examples of preservatives include sodium benzoate, sorbic acid and esters of p-hydroxybenzoic acid. Antioxidants and suspending agents may be also used.

For some embodiments, the agents of the present invention may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e. g. as a carrier, diluent or solubiliser. Alpha-, beta- and gamma-cyclodextrins are most commonly used and suitable examples are described in WO 91/11172, WO 94/02518 and WO 98/55148.

The compounds of the invention may be milled using known milling procedures such as wet milling to obtain a particle size appropriate for tablet formation and for other formulation types. Finely divided (nanoparticulate) preparations of the compounds of the invention may be prepared by processes known in the art, for example see WO 02/00196 (SmithKline Beecham).

There may be different composition/formulation requirements dependent on the different delivery systems. By way of example, the pharmaceutical composition of the present invention may be formulated to be delivered using a minipump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be delivered by both routes.

Where the agent is to be delivered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

The routes for administration (delivery) include, but are not limited to, one or more of: oral (e. g. as a tablet, capsule, or as an ingestable solution), topical, mucosal (e. g. as a nasal spray or aerosol for inhalation), nasal, parenteral (e. g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, epidural and sublingual. It is to be understood that not all of the compounds need be administered by the same route. Likewise, if the composition comprises more than one active component, then those components may be administered by different routes.

The compounds of formula (I) and their pharmaceutically acceptable salts and solvates may be formulated for administration in any suitable manner. They may, for example, be formulated for topical administration or administration by inhalation or, more preferably, for oral, transdermal or parenteral administration. The pharmaceutical composition may be in a form such that it can effect controlled release of the compounds of formula (I) and their pharmaceutically acceptable derivatives. In a preferred embodiment, the agents of the present invention are delivered systemically such as orally, buccally or sublingually. A particularly preferred method of administration, and corresponding formulation, is oral administration.

For oral administration, the pharmaceutical composition may take the form of, and be administered as, for example, tablets (including sub-lingual tablets) and capsules (each including timed release and sustained release formulations), ovules, pills, powders, granules, elixirs, tinctures, emulsions, solutions, syrups or suspensions prepared by conventional means with acceptable excipients for immediate-, delayed, modified-, sustained-, pulsed- or controlled release.

For instance, for oral administration in the form of a tablet or capsule, the active drug component can be combined with an oral, non-toxic pharmaceutically acceptable inert carrier such as ethanol, glycerol, water and the like. The tablets may also contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavouring agents, colouring matter or dyes, with emulsifying and/or suspending agents and with diluents such as water, ethanol, propylene glycol and glycerin, and combinations thereof.

Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules can be made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders Include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as-carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of the present invention can also be administered in the form of liposome emulsion delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolyl-ysine substituted with palmitoyl residues. Furthermore, the compounds of the present invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

The present invention includes pharmaceutical compositions containing 0.1 to 99.5%, more particularly, 0.5 to 90% of a compound of the formula (I) in combination with a pharmaceutically acceptable carrier.

Likewise, the composition may also be administered in nasal, ophthalmic, otic, rectal, topical, intravenous (both bolus and infusion), intraperitoneal, intraarticular, subcutaneous or intramuscular, inhalation or insufflation form, all using forms well known to those of ordinary skill in the pharmaceutical arts.

For transdermal administration, the pharmaceutical composition may be given in the form of a transdermal patch, such as a transdermal iontophoretic patch.

If the compound of the present invention is administered parenterally, then examples of such administration include one or more of: intravenously, intraarterially, intraperitoneally, intrathecally, intraventricularly, intraurethrally, intrasternally, intracranially, intramuscularly or subcutaneously administering the agent; and/or by using infusion techniques. For parenteral administration, the pharmaceutical composition may be given as an injection or a continuous infusion (e.g. intravenously, intravascularly or subcutaneously). The compositions may take such forms as suspensions, solutions or emulsions in oily or aqueous vehicles and may contain formulatory agents such as suspending, stabilizing and/or dispersing agents. For administration by injection these may take the form of a unit dose presentation or as a multidose presentation preferably with an added preservative. Alternatively for parenteral administration the active ingredient may be in powder form for reconstitution with a suitable vehicle. For parenteral administration, the compound is best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

The compositions of the present invention may be administered by direct injection.

The compounds of the invention may also be formulated as a depot preparation. Such long acting formulations may be administered by implantation (for example subcutaneously or intramuscularly) or by intramuscular injection.

Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

Alternatively the composition may be formulated for topical application, for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For application topically to the skin, the agent of the present invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water.

Alternatively, it can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

For administration by inhalation the compounds according to the invention are conveniently delivered in the form of an aerosol spray presentation from pressurized packs or a nebulizer, with the use of a suitable propellant, e.g. dichlorodifluoromethane, trichlorofluoromethane, dichlorotetrafluoroethane, a hydrofluoroalkane such as tetrafluoroethane or heptafluoropropane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

Alternatively, the compound of the present invention can be administered in the form of a suppository or pessary, or it may be applied topically in the form of a gel, hydrogel, lotion, solution, cream, ointment or dusting powder.

The compounds of the present invention may also be administered by the pulmonary or rectal routes. They may also be administered by the ocular route. For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

The pharmaceutical compositions generally are administered in an amount effective for treatment or prophylaxis of a specific condition or conditions. Initial dosing in human is accompanied by clinical monitoring of symptoms, such symptoms for the selected condition. In general, the compositions are administered in an amount of active agent of at least about 100 μg/kg body weight. In most cases they will be administered in one or more doses in an amount not in excess of about 20 mg/kg body weight per day. Preferably, in most cases, dose is from about 100 μg/kg to about 5 mg/kg body weight, daily. For administration particularly to mammals, and particularly humans, it is expected that the daily dosage level of the active agent will be from 0. 1 mg/kg to 10 mg/kg and typically around 1 mg/kg. It will be appreciated that optimum dosage will be determined by standard methods for each treatment modality and indication, taking into account the indication, its severity, route of administration, complicating conditions and the like. The physician in any event will determine the actual dosage which will be most suitable for an individual and will vary with the activity of the specific compound to be employed, the metabolic stablity and length of action of that compound, age, weight, general health, sex, diet, mode and time of administration, rate of excretion, drug combination, severity of the particular condition and response of the particular individual. The effectiveness of a selected actual dose can readily be determined, for example, by measuring clinical symptoms or standard anti-inflammatory indicia after administration of the selected dose. The above dosages are exemplary of the average case. There can, of course, be individual instances where higher or lower dosage ranges are merited, and such are within the scope of this invention. For conditions or disease states as are treated by the present invention, maintaining consistent daily levels in a subject over an extended period of time, e.g., in a maintenance regime, can be particularly beneficial. For oral and parenteral administration to humans, the daily dosage level of the agent may be in single or divided doses In another aspect, the present invention provides a compound of formula (I) or a pharmaceutically acceptable derivative thereof, for use in therapy.

The compounds of the present invention are generally inhibitors of the serine/threonine kinase p38 and are therefore also inhibitors of cytokine production which is mediated by p38 kinase. Within the meaning of the term "inhibitors of the serine/threonine kinase p38" are included those compounds that interfere with the ability of p38 to transfer a phosphate group from ATP to a protein substrate according to the assay described below.

It will be appreciated that the compounds of the invention may be selective for one or more of the isoforms of p38, for example p38α, p38β, p38γ and/or p38δ. In one embodiment, the compounds of the invention selectively inhibit the p38α isoform. In another embodiment, the compounds of the invention selectively inhibit the p38β isoform. In a further embodiment, the compounds of the invention selectively inhibit the p38α and p38β isoforms. Assays for determining the selectivity of compounds for the p38 isoforms are described in, for example, WO 99/61426, WO 00/71535 and WO 02/46158.

It is known that p38 kinase activity can be elevated (locally or throughout the body), p38 kinase can be incorrectly temporally active or expressed, p38 kinase can be expressed or active in an inappropriate location, p38 kinase can be constitutively expressed, or p38 kinase expression can be erratic; similarly, cytokine production mediated by p38 kinase activity can be occurring at inappropriate times, inappropriate locations, or it can occur at detrimentally high levels.

Accordingly, the present invention provides a method for the treatment of a condition or disease state mediated by p38 kinase activity, or mediated by cytokines produced by the activity of p38 kinase, in a subject which comprises administering to said subject a therapeutically effective amount of a compound of formula (I) or a pharmaceutically acceptable derivative thereof. The compound may be administered as a single or polymorphic crystalline form or forms, an amorphous form, a single enantiomer, a racemic mixture, a single stereoisomer, a mixture of stereoisomers, a single diastereoisomer or a mixture of diastereoisomers.

The present invention also provides a method of inhibiting cytokine production which is mediated by p38 kinase activity in a subject, e.g. a human, which comprises administering to said subject in need of cytokine production inhibition a therapeutic, or cytokine-inhibiting, amount of a compound of the present invention. The compound may be administered as a single or polymorphic crystalline form or forms, an amorphous form, a single enantiomer, a racemic mixture, a single stereoisomer, a mixture of stereoisomers, a single diastereoisomer or a mixture of diastereoisomers.

The present invention treats these conditions by providing a therapeutically effective amount of a compound of this invention. By "therapeutically effective amount" is meant a symptom-alleviating or symptom-reducing amount, a cytokine-reducing amount, a cytokine-inhibiting amount, a kinase-regulating amount and/or a kinase-inhibiting amount of a compound. Such amounts can be readily determined by standard methods, such as by measuring cytokine levels or observing alleviation of clinical symptoms. For example, the clinician can monitor accepted measurement scores for anti-inflammatory treatments. It will be appreciated that reference to treatment includes acute treatment or prophylaxis as well as the alleviation of established symptoms.

The compounds of the present invention can be administered to any subject in need of inhibition or regulation of p38 kinase or in need of inhibition or regulation of p38 mediated cytokine production. In particular, the compounds may be administered to mammals. Such mammals can include, for example, horses, cows, sheep, pigs, mice, dogs, cats, primates such as chimpanzees, gorillas, rhesus monkeys, and, most preferably, humans.

Thus, the present invention provides methods of treating or reducing symptoms in a human or animal subject suffering from, for example, rheumatoid arthritis, osteoarthritis, asthma, psoriasis, eczema, allergic rhinitis, allergic conjunctivitis, adult respiratory distress syndrome, chronic pulmonary inflammation, chronic obstructive pulmonary disease, chronic heart failure, silicosis, endotoxemia, toxic shock syndrome, inflammatory bowel disease, tuberculosis, atherosclerosis, neurodegenerative disease, Alzheimer's disease, Parkinson's disease, Huntington's disease, amyotrophic lateral sclerosis, epilepsy, multiple sclerosis, aneurism, stroke, irritable bowel syndrome, muscle degeneration, bone resorption diseases, osteoporosis, diabetes, reperfusion injury, graft vs. host reaction, allograft rejections, sepsis, systemic cachexia, cachexia secondary to infection or malignancy, cachexia secondary to aquired immune deficiency syndrome (AIDS), malaria, leprosy, infectious arthritis, leishmaniasis, Lyme disease, glomerulonephritis, gout, psoriatic arthritis, Reiter's syndrome, traumatic arthritis, rubella arthritis, Crohn's disease, ulcerative colitis, acute synovitis, gouty arthritis, spondylitis, and non articular inflammatory conditions, for example, herniated/ruptured/prolapsed intervertebral disk syndrome, bursitis, tendonitis, tenosynovitis, fibromyalgic syndrome and other inflammatory conditions associated with ligamentous sprain and regional musculoskeletal strain, pain, for example that associated with inflammation and/or trauma, osteopetrosis, restenosis, thrombosis, angiogenesis, cancer including breast cancer, colon cancer, lung cancer or prostatic cancer, which comprises administering to said subject a therapeutically effective amount of a compound of formula (I) or a pharmaceutically acceptable derivative thereof.

A further aspect of the invention provides a method of treatment of a human or animal subject suffering from rheumatoid arthritis, asthma, psoriasis, chronic pulmonary inflammation, chronic obstructive pulmonary disease, chronic heart failure, systemic cachexia, glomerulonephritis, Crohn's disease, neurodegenerative disease, Alzheimer's disease, Parkinson's disease, epilepsy and cancer including breast cancer, colon cancer, lung cancer and prostatic cancer, which comprises administering to said subject a therapeutically effective amount of a compound of formula (I) or a pharmaceutically acceptable derivative thereof.

A further aspect of the invention provides a method of treatment of a human or animal subject suffering from rheumatoid arthritis, asthma, psoriasis, chronic pulmonary inflammation, chronic obstructive pulmonary disease, chronic heart failure, systemic cachexia, glomerulonephritis, Crohn's disease and cancer including breast cancer, colon cancer, lung cancer and prostatic cancer, which comprises administering to said subject a therapeutically effective amount of a compound of formula (I) or a pharmaceutically acceptable derivative thereof.

A further aspect of the invention provides a method of treatment of a human or animal subject suffering from rheumatoid arthritis, asthma, chronic pulmonary inflammation, chronic obstructive pulmonary disease, neurodegenerative disease, Alzheimer's disease, Parkinson's disease and epilepsy which comprises administering to said subject a therapeutically effective amount of a compound of formula (I) or a pharmaceutically acceptable derivative thereof.

A further aspect of the invention provides a method of treatment of a human or animal subject suffering from any type of pain including chronic pain, rapid onset of analgesis, neuromuscular pain, headache, cancer pain, acute and chronic inflammatory pain associated with osteoarthritis and rheumatoid arthritis, post operative inflammatory pain, neuropathic pain, diabetic neuropathy, trigeminal neuralgia, post-hepatic neuralgia, inflammatory neuropathies and migraine pain which comprises administering to said subject a therapeutically effective amount of a compound of formula (I) or a pharmaceutically acceptable derivative thereof.

A further aspect of the invention provides the use of a compound of formula (I), or a pharmaceutically acceptable derivative thereof, in the manufacture of a medicament for use in the treatment of a condition or disease state mediated by p38 kinase activity or mediated by cytokines produced by p38 kinase activity.

The compounds of formula (I) and their derivatives may be employed alone or in combination with other therapeutic agents for the treatment of the above-mentioned conditions. The invention thus provides, in a further aspect, a combination comprising a compound of the invention or a pharmaceutically accpetable derivative thereof together with a further therapeutic agent.

In particular, in rheumatoid arthritis therapy, combination with other chemotherapeutic or antibody agents is envisaged. Combination therapies according to the present invention thus comprise the administration of at least one compound of formula (I) or a pharmaceutically acceptable salt or solvate thereof and at least one other pharmaceutically active agent. The compound(s) of formula (I) or pharmaceutically acceptable salt(s) or solvate(s) thereof and the other pharmaceutically active agent(s) may be administered together or separately and, when administered separately, this may occur separately or sequentially in any order. The amounts of the compound(s) of formula (I) or pharmaceutically acceptable salt(s) or solvate(s) thereof and the other pharmaceutically active agent(s) and the relative timings of administration will be selected in order to achieve the desired combined therapeutic effect. Appropriate doses will be readily appreciated by those skilled in the art. It will be appreciated that the amount of a compound of the invention required for treatment will vary with the nature of the condition being treated and the age and condition of the patient and will ultimately be at the discretion of the attendant physician or veterinarian. Examples of other pharmaceutically active agents which may be employed in combination with compounds of formula (I) and their salts and solvates for rheumatoid arthritis therapy include: immunosuppresants such as amtolmetin guacil, mizoribine and rimexolone; anti-TNFα agents such as etanercept, infliximab, diacerein; tyrosine kinase inhibitors such as leflunomide; kallikrein antagonists such as subreum; interleukin 11 agonists such as oprelvekin; interferon beta 1 agonists; hyaluronic acid agonists such as NRD-101 (Aventis); interleukin 1 receptor antagonists such as anakinra; CD8 antagonists such as amiprilose hydrochloride; beta amyloid precursor protein antagonists such as reumacon; matrix metalloprotease inhibitors such as cipemastat and other disease modifying anti-rheumatic drugs (DMARDs) such as methotrexate, sulphasalazine, cyclosporin A, hydroxychoroquine, auranofin, aurothioglucose, gold sodium thiomalate and penicillamine.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention.

The individual components of such combinations may be administered either sequentially or simultaneously in separate or combined pharmaceutical formulations by any convenient route.

When administration is sequential, either the compound of the invention or the second therapeutic agent may be administered first. When administration is simultaneous, the combination may be administered either in the same or different pharmaceutical composition.

When combined in the same formulation it will be appreciated that the two compounds must be stable and compatible with each other and the other components of the formulation. When formulated separately they may be provided in any convenient formulation, conveniently in such manner as are known for such compounds in the art.

EXAMPLES

The following examples are illustrative embodiments of the invention, not limiting the scope of the invention in any way. Reagents are commercially available or are prepared according to procedures in the literature.

LCMS was conducted on a column (3.3 cm×4.6 mm ID, 3 um ABZ+PLUS), at a Flow Rate of 3 ml/min, Injection Volume of 5 μl, at room temperature and UV Detection Range at 215 to 330 nm.

Intermediate 1: 2-Aminobenzyl-2-cyclopropylethanol

Sodium triacetoxyborohydride (51 g) was added to a solution of 1-cyclopropyl-2-hydroxyethanone (16.0 g), benzylamine (17.5 ml) and acetic acid (9.15 ml) in THF (300 ml) keeping the temperature at 25-30° C. After stirring for 24 hours the mixture was evaporated, treated with saturated sodium bicarbonate (250 ml) and extracted with ethyl acetate (10×200 ml). The combined organic extracts were dried (sodium sulphate) and evaporated. The residual oil gained was purified by flash chromatography (Silica, Merck 9385), eluting with DCM:ethanol:ammonia (967:30:3 to 945:50:5) to give 2-aminobenzyl-2-cyclopropylethanol (10.63 g).

NMR: δH[$^2$H$_3$]-Chloroform 7.32 (5H, m), 3.92 (1H, d), 3.82 (1H, d), 3.73 (1H, dd), 3.49 (1H, dd), 1.90 (1H, m), 0.83 (1H, m), 0.60 (1H, m), 0.47 (1H, m), 0.22 (1H, m), 0.13 (1H, m).

Intermediate 2: 2-Amino-2-cyclopropylethanol

A solution of 2-aminobenzyl-2-cyclopropylethanol (Intermediate 1) (10.6 g) in ethanol (100 ml) was stirred with Pd/C (5% loading, 3 g) in a hydrogen atmosphere at 23° C. for 4 days. The catalyst was removed by filtration and the filtrate evaporated to give 2-amino-2-cyclopropylethanol.

General Method

A solution of the acid (50 mg) in DMF (1 ml) was treated with HATU (65 mg) at room temperature. DIPEA (87 uL) was added. After 5 minutes this was added to a solution of the amine (0.17 mmol) in DMF (1 ml). The reaction mixtures were left at room temperature for 16 hrs, then concentrated in vacuo. The residues were dissolved in chloroform (1.5 ml) and each was loaded onto an aminopropyl SPE cartridge (1 g) that had been pre-equilibrated with chloroform. The cartridge was then eluted with, chloroform (2.5 ml), ethyl acetate/methanol (9:1, 2.5 ml). The fractions containing product were isolated by evaporation.

| Example | Amine | Retention Time (mins) | MH+ |
|---|---|---|---|
| Example 1 4'-(azetidin-1-ylcarbonyl)-N-cyclopropyl-5-fluoro-6-methyl-1,1'-biphenyl-3-carboxamide | azetidine | 2.87 | 353 |

| Example | Amine | Retention Time (mins) | MH+ |
|---|---|---|---|
| Example 2<br>$N^{4'}$-(2-cyanoethyl)-$N^3$-cyclopropyl-5-fluoro-6-methyl-1,1'-biphenyl-3,4'-dicarboxamide<br>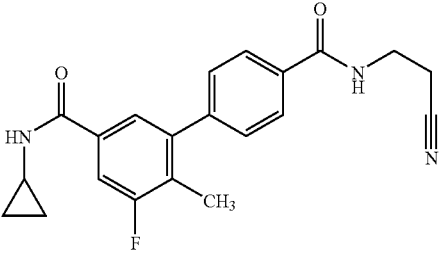 | 3-aminopropionitrile | 2.82 | 366 |
| Example 3<br>$N^3$-cyclopropyl-5-fluoro-6-methyl-$N^{4'}$-(1,1,3-trimethyl-2-oxobutyl)-1,1'-biphenyl-3,4'-dicarboxamide<br>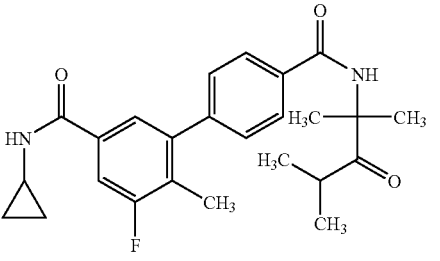 | 2-amino-2,4-dimethyl-3-pentanone | 3.26 | 425 |
| Example 4<br>N-cyclopropyl-5-fluoro-6-methyl-4'-(pyrrolidin-1-ylcarbonyl)-1,1'-biphenyl-3-carboxamide<br>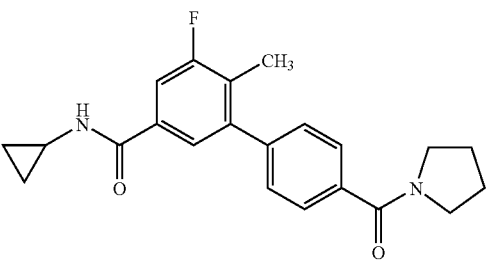 | pyrrolidine | 2.96 | 367 |
| Example 5<br>$N^3$-cyclopropyl-$N^{4'}$-(1,1-dimethyl-3-oxobutyl)-5-fluoro-6-methyl-1,1'-biphenyl-3,4'-dicarboxamide<br>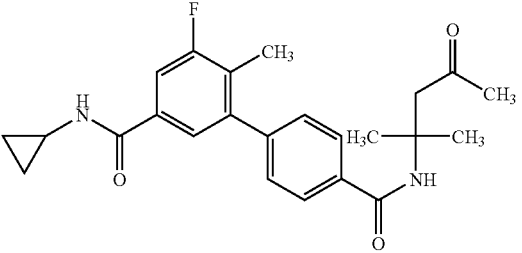 | 4-amino-4-methyl-2-pentanone | 3.06 | 411 |

-continued

| Example | Amine | Retention Time (mins) | MH+ |
|---|---|---|---|
| Example 6<br>$N^{4'}$-(1-cyanocyclohexyl)-$N^3$-cyclopropyl-5-fluoro-6-methyl-1,1'-biphenyl-3,4'-dicarboxamide<br>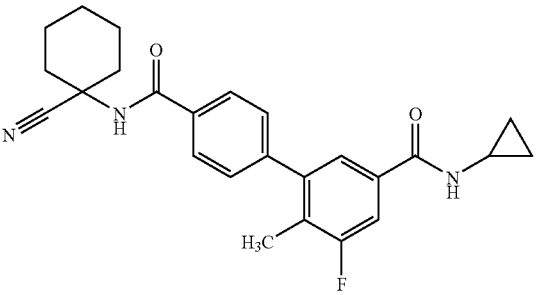 | 1-cyanocyclohexylamine | 3.27 | 420 |
| Example 7<br>$N^{4'}$-(1-cyano-1-methylpropyl)-$N^3$-cyclopropyl-5-fluoro-6-methyl-1,1'-biphenyl-3,4'-dicarboxamide<br>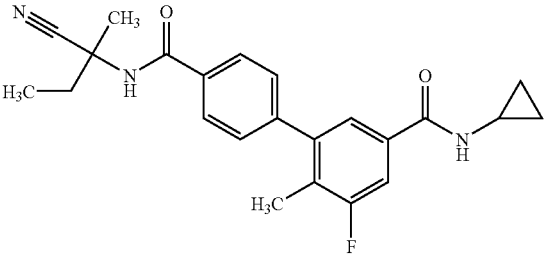 | 2-amino-2-methylbutyronitrile | 3.12 | 394 |
| Example 8<br>$N^3$-cyclopropyl-5-fluoro-6-methyl-$N^{4'}$-[2-(methylsulfonyl)ethyl]-1,1'-biphenyl-3,4'-dicarboxamide<br>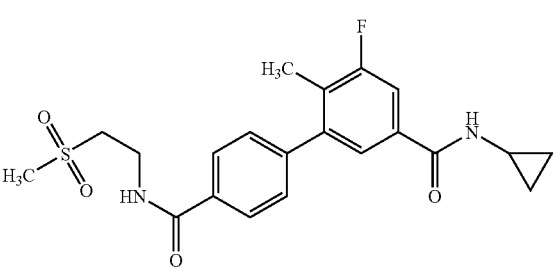 | 2-methanesulphonylethylamine | 2.83 | 419 |
| Example 9<br>$N^3$-cyclopropyl-5-fluoro-$N^{4'}$-[(1-hydroxycyclohexyl)methyl]-6-methyl-1,1'-biphenyl-3,4'-dicarboxamide<br>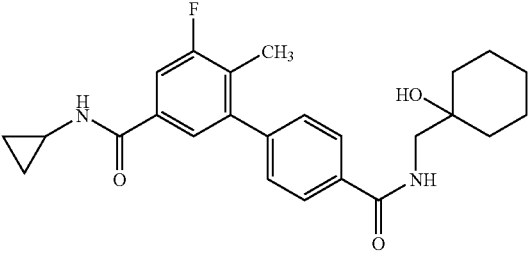 | (1-hydroxycyclohexyl)methyl amine | 3.07 | 425 |

-continued

| Example | Amine | Retention Time (mins) | MH+ |
|---|---|---|---|
| Example 10<br>$N^3$-cyclopropyl-$N^{4'}$-(1-cyclopropyl-2-hydroxyethyl)-5-fluoro-6-methyl-1,1'-biphenyl-3,4'-dicarboxamide | 2-amino-2-cyclopropylethanol | 2.84 | 397 |
| Example 11<br>$N^3$-cyclopropyl-5-fluoro-6-methyl-$N^{4'}$-[2-(methylthio)ethyl]-1,1'-biphenyl-3,4'-dicarboxamide | 2-(methylthio)ethylamine | 3.15 | 387 |

Abbreviations

DIPEA N,N-Diisopropylethylamine
DMF Dimethylformamide
HATU O-(7-Azabenzotriazol-1-yl)-N,N,N',N'-tetramethyluronium hexafluorophosphate
SPE Solid phase extraction Biological Examples The activity of compounds of formula (I) as p38 inhibitors may be determined by the following in vitro assays:

Fluorescence Anisotropy Kinase Binding Assay

The kinase enzyme, fluorescent ligand and a variable concentration of test compound are incubated together to reach thermodynamic equilibrium under conditions such that in the absence of test compound the fluorescent ligand is significantly (>50%) enzyme bound and in the presence of a sufficient concentration (>10×$K_i$) of a potent inhibitor the anisotropy of the unbound fluorescent ligand is measurably different from the bound value.

The concentration of kinase enzyme should preferably be $\geq 1 \times K_f$. The concentration of fluorescent ligand required will depend on the instrumentation used, and the fluorescent and physicochemical properties. The concentration used must be lower than the concentration of kinase enzyme, and preferably less than half the kinase enzyme concentration. A typical protocol is:

All components dissolved in Buffer of final composition 62.5 mM HEPES, pH 7.5, 1.25 mM CHAPS, 1.25 mM DTT, 12.5 mM $MgCl_2$ 3.3% DMSO.

p38 Enzyme concentration: 12 nM
Fluorescent ligand concentration: 5 nM
Test compound concentration: 0.1 nM-100 uM
Components incubated in 30 ul final volume in NUNC 384 well black microtitre plate until equilibrium reached (5-30 mins)
Fluorescence anisotropy read in LJL Acquest.

Definitions:
$K_i$=dissociation constant for inhibitor binding
$K_f$=dissociation constant for fluorescent ligand binding
The fluorescent ligand is the following compound:

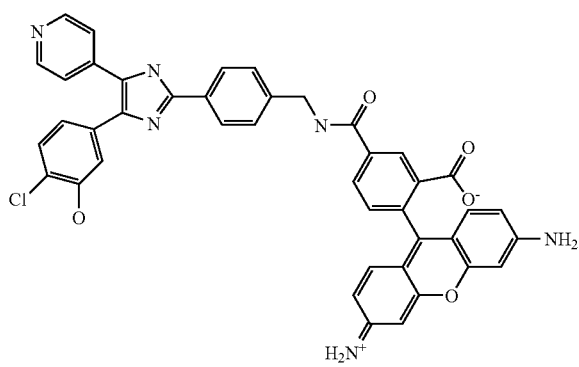

which is derived from 5-[2-(4-aminomethylphenyl)-5-pyridin-4-yl-1H-imidazol-4-yl]-2-chlorophenol and rhodamine green.

Results

The compounds described in the Examples were tested as described above and had $IC_{50}$ values of <10 μM.

The application of which this description and claims forms part may be used as a basis for priority in respect of any subsequent application. The claims of such subsequent application may be directed to any feature or combination of features described herein. They may take the form of product, composition, process or use claims and may include, by way of example and without limitation, one or more of the following claims:

The invention claimed is:
1. A compound of formula (I):

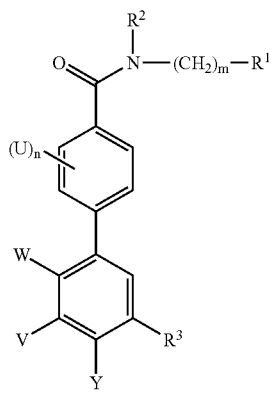

wherein
R$^1$ is selected from C$_{1-6}$alkyl substituted by one to three groups independently selected from oxo, cyano and —S(O)$_p$R$^4$, and C$_{3-7}$cycloalkyl substituted by one to three groups independently selected from oxo, cyano, —S(O)$_p$R$^4$, OH, halogen, C$_{1-6}$alkoxy, —NR$^5$R$^6$, —CONR$^5$R$^6$, —NCOR$^5$, —COOR$^5$, —SO$_2$NR$^5$R$^6$, —NHSO$_2$R$^5$ and —NHCONHR$^5$, R$^2$ is selected from hydrogen, C$_{1-6}$alkyl and —(CH$_2$)$_q$—C$_{3-7}$cycloalkyl, or (CH$_2$)$_m$R$^1$ and R$^2$, together with the nitrogen atom to which they are bound, form a four- to six-membered heterocyclic ring optionally containing one or two additional heteroatoms independently selected from oxygen, sulphur and N—R$^7$, wherein the ring is optionally substituted by one or two groups independently selected from oxo, C$_{1-6}$alkyl, halogen and trifluoromethyl;

R$^3$ is the group —CO—NH—(CH$_2$)$_r$—R$^8$ or —NH—CO—R$^9$;

R$^4$ is selected from hydrogen, C$_{1-6}$alkyl, heterocyclyl optionally substituted by C$_{1-4}$alkyl, and phenyl wherein the phenyl is optionally substituted by up to two groups independently selected from C$_{1-6}$alkoxy, C$_{1-6}$alkyl and halogen;

R$^5$ is selected from hydrogen, C$_{1-6}$alkyl and phenyl wherein the phenyl group is optionally substituted by up to two substituents selected from C$_{1-6}$alkyl and halogen, R$^6$ is selected from hydrogen and C$_{1-6}$alkyl, or R$^5$ and R$^6$, together with the nitrogen atom to which they are bound, form a five- to six-membered heterocyclic or heteroaryl ring optionally containing up to one additional heteroatom selected from oxygen, sulfur and nitrogen, wherein the ring is optionally substituted by up to two C$_{1-6}$alkyl groups;

R$^7$ is selected from hydrogen and methyl;

when r is 0 to 2, R$^8$ is selected from hydrogen, C$_{1-6}$alkyl, C$_{3-7}$cycloalkyl, CONHR$^5$, phenyl optionally substituted by R$^{10}$ and/or R$^{11}$, heteroaryl optionally substituted by R$^{10}$ and/or R$^{11}$ and heterocyclyl optionally substituted by R$^{10}$ and/or R$^{11}$, and when r is 2, R$^8$ is additionally selected from C$_{1-6}$alkoxy, NHCOR$^5$, NHCONHR$^5$, NR$^5$R$^6$ and OH;

R$^9$ is selected from hydrogen, C$_{1-6}$alkyl, C$_{1-6}$alkoxy, —(CH$_2$)$_s$—C$_{3-7}$cycloalkyl, trifluoromethyl, —(CH$_2$)$_t$phenyl optionally substituted by R$^{12}$ and/or R$^{13}$, —(CH$_2$)$_t$heteroaryl optionally substituted by R$^{12}$ and/or R$^{13}$, —(CH$_2$)$_t$heterocyclyl optionally substituted by R$^{12}$ and/or R$^{13}$ and —(CH$_2$)$_t$fused bicyclyl optionally substituted by R$^{12}$ and/or R$^{13}$;

R$^{10}$ is selected from C$_{1-6}$alkyl, C$_{1-6}$alkoxy, —CONR$^6$R$^{14}$, —NHCOR$^{14}$, —SO$_2$NHR$^{14}$, —NHSO$_2$R$^{14}$, halogen, trifluoromethyl, —X—(CH$_2$)$_j$-phenyl optionally substituted by one or more halogen atoms or C$_{1-6}$alkyl groups, —X—(CH$_2$)$_j$-heterocyclyl or —X—(CH$_2$)$_j$-heteroaryl wherein the heterocyclyl or heteroaryl group is optionally substituted by one or more substituents selected from C$_{1-6}$alkyl, R$^{11}$ is selected from C$_{1-6}$alkyl and halogen, or when R$^{10}$ and R$^{11}$ are ortho substituents, then together with the carbon atoms to which they are bound, R$^{10}$ and R$^{11}$ may form a five- or six-membered saturated or unsaturated ring to give a fused bicyclic ring system, wherein the ring that is formed by R$^{10}$ and R$^{11}$ optionally contains one or two heteroatoms selected from oxygen, nitrogen and sulfur;

R$^{12}$ is selected from C$_{1-6}$alkyl, C$_{1-6}$alkoxy, —(CH$_2$)$_s$—C$_{3-7}$cycloalkyl, —CONR$^{15}$R$^{16}$, —NHCOR$^{16}$, —SO$_2$NHR$^{15}$, —NHSO$_2$R$^{16}$, halogen, —(CH$_2$)$_k$NR$^{17}$R$^{18}$, oxy, trifluoromethyl, phenyl optionally substituted by one or more R$^{13}$ groups and heteroaryl wherein the heteroaryl is optionally substituted by one or more R$^{13}$ groups, R$^{13}$ is selected from C$_{1-6}$alkyl, C$_{1-6}$alkoxy, halogen, trifluoromethyl and —NR$^{17}$R$^{18}$, or R$^{12}$ and R$^{13}$, together with the carbon atoms to which they are bound, form a five- or six-membered saturated or unsaturated ring to give a fused bicyclic ring system, wherein the ring that is formed by R$^{12}$ and R$^{13}$ optionally contains one or two heteroatoms selected from oxygen, nitrogen and sulfur;

R$^{14}$ is selected from hydrogen and C$_{1-6}$alkyl;

R$^{15}$ is selected from hydrogen, C$_{1-6}$alkyl and phenyl wherein the phenyl group may be optionally substituted by one or more R$^{13}$ groups, R$^{16}$ is selected from hydrogen and C$_{1-6}$alkyl, or R$^{15}$ and R$^{16}$, together with the nitrogen atom to which they are bound, form a five- to six-membered heterocyclic ring optionally containing one additional heteroatom selected from oxygen, sulfur and N—R$^7$, wherein the ring is optionally substituted by up to two C$_{1-6}$alkyl groups;

R$^{17}$ is selected from hydrogen, C$_{1-6}$alkyl and —(CH$_2$)$_s$—C$_{3-7}$cycloalkyl optionally substituted by C$_{1-6}$alkyl, R$^{18}$ is selected from hydrogen and C$_{1-6}$alkyl, or R$^{17}$ and R$^{18}$, together with the nitrogen atom to which they are bound, form a three- to seven-membered heterocyclic ring optionally containing one additional heteroatom selected from oxygen, sulfur and N—R$^7$, wherein the ring may contain up to one double bond and the ring is optionally substituted by one or more $R^{19}$ groups;

$R^{19}$ is selected from $C_{1-6}$alkyl, oxy, —$CH_2OC_{1-6}$alkyl, trichloromethyl and —$N(C_{1-6}alkyl)_2$;

X is selected from —O— and a bond;

U is selected from methyl and halogen;

W is selected from methyl and chlorine;

V and Y are each selected independently from hydrogen, methyl and halogen;

m is selected from 0, 1, 2, 3 and 4 at least one carbon atom of the resulting carbon chain is optionally substituted with one or two groups selected independently from $C_{1-6}$alkyl, and wherein the $C_{1-6}$alkyl group is optionally substituted by up to three OH groups;

n, p, r and j are independently selected from 0, 1 and 2;

q and k are independently selected from 0, 1, 2 and 3; and s and t are independently selected from 0 and 1;

or a pharmaceutically acceptable derivative thereof.

2. A compound according to claim 1 wherein $R^1$ is selected from $C_{2-6}$alkyl substituted by one or two groups independently selected from oxo, cyano and —$S(O)_rR^4$, and $C_{3-6}$cycloalkyl optionally substituted by one or two groups independently selected from OH and cyano.

3. A compound according to claim 1 wherein $R^2$ is hydrogen.

4. A compound according to claim 1 wherein $R^8$ is $C_{3-6}$cycloalkyl.

5. A compound according to claim 1 wherein m is selected from 0 and 1 and wherein the carbon chain is optionally substituted by one or two methyl groups which are optionally substituted by OH.

6. A compound according to claim 1 as defined in any one of Examples 1 to 11, or a pharmaceutically acceptable derivative thereof.

7. A process for preparing a compound according to claim 1 which comprises:

(a) reacting a compound of formula (XXII)

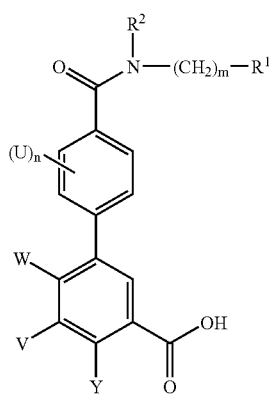

(XXII)

wherein $R^1$, $R^2$, U, W, V, Y, m and n are as defined in claim 1, with a compound of formula (XXIII)

$R^8$—$(CH_2)_r$—$NH_2$ (XXIII)

wherein $R^8$ and r are as defined in claim 1, under amide forming conditions optionally converting the acid compound (XXII) to an activated form of the acid before reaction with the amine compound (XXIII);

(b) reacting a compound of formula (XXIV)

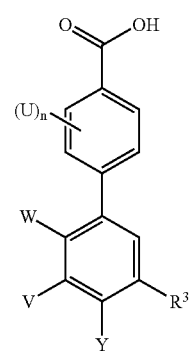

(XXIV)

wherein $R^3$, U, W, V, Y and n are as defined in claim 1, with a compound of formula (XXV)

$R^1(CH_2)_mNR^2H$ (XXV)

wherein $R^1$, $R^2$, m and n are as defined in claim 1, under amide forming conditions;

(c) reacting a compound of formula (XXVI)

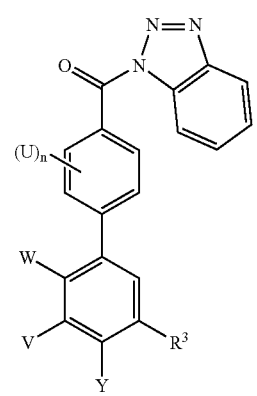

(XXVI)

wherein $R^3$, U, W, V, Y and n are as defined in claim 1, with a compound of formula (XXV) as defined above;

(d) reacting a compound of formula (XXVII)

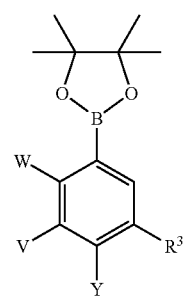

(XXVII)

wherein W, V, Y and $R^3$ are as defined in claim 1, with a compound of formula (XXVIII)

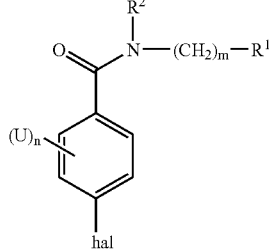

wherein R$^1$, R$^2$, U, m and n are as defined above and hal is halogen, in the presence of a catalyst; or (e) reacting a compound of formula (XXIX)

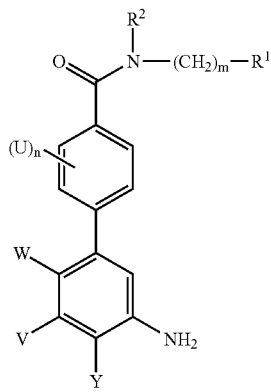

wherein R$^1$, R$^2$, U, W, V, Y, m and n are as defined in claim 1, with a compound of formula (XXX)

R$^9$CO$_2$H    (XXX)

wherein R$^9$ is as defined in claim 1, under amide forming conditions optionally converting the acid compound (XXX) to an activated form of the acid before reaction with the amine compound (XXIX).

8. A pharmaceutical composition comprising at least one compound according to claim 1 or a pharmaceutically acceptable derivative thereof, in association with one or more pharmaceutically acceptable excipients, diluents and/or carriers.

9. A compound according to claim 1 wherein R$^3$ is the group —CO—NH—(CH$_2$)$_r$—R$^8$.

10. A compound according to claim 9 wherein R$^8$ is selected from C$_{1-4}$alkyl or C$_{3-6}$cycloalkyl, CONHR$^5$, phenyl optionally substituted by R$^{10}$ and/or R$^{11}$, thiazolyl, pyrazolyl, thiadiazolyl, or pyridyl all optionally substituted by R$^{10}$ and/or R$^{11}$.

11. A compound of formula (I):

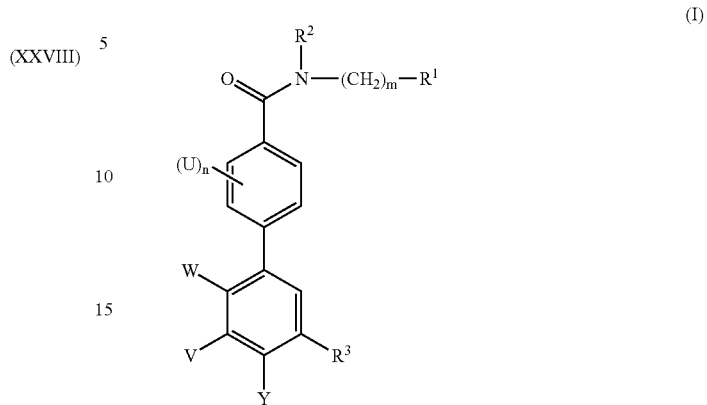

wherein
R$^1$ is a C$_{3-7}$cycloalkyl;
R$^2$ is selected from hydrogen, C$_{1-6}$alkyl and —(CH$_2$)$_q$—C$_{3-7}$cycloalkyl, or
(CH$_2$)$_m$R$^1$ and R$^2$, together with the nitrogen atom to which they are bound, form a four- to six-membered heterocyclic ring optionally containing one or two additional heteroatoms independently selected from oxygen, sulphur and N—R$^7$, wherein the ring is optionally substituted by one or two groups independently selected from oxo, C$_{1-6}$alkyl, halogen and trifluoromethyl;
R$^3$ is the group —CO—NH—(CH$_2$)$_r$—R$^8$ or —NH—CO—R$^9$;
R$^4$ is selected from hydrogen, C$_{1-6}$alkyl, heterocyclyl optionally substituted by C$_{1-4}$alkyl, and phenyl wherein the phenyl is optionally substituted by up to two groups independently selected from C$_{1-6}$alkoxy, C$_{1-6}$alkyl and halogen;
R$^5$ is selected from hydrogen, C$_{1-6}$alkyl and phenyl wherein the phenyl group is optionally substituted by up to two substituents selected from C$_{1-6}$alkyl and halogen,
R$^6$ is selected from hydrogen and C$_{1-6}$alkyl, or
R$^5$ and R$^6$, together with the nitrogen atom to which they are bound, form a five- to six-membered heterocyclic or heteroaryl ring optionally containing up to one additional heteroatom selected from oxygen, sulfur and nitrogen, wherein the ring is optionally substituted by up to two C$_{1-6}$alkyl groups;
R$^7$ is selected from hydrogen and methyl;
when r is 0 to 2, R$^8$ is selected from hydrogen, C$_{1-6}$alkyl, C$_{3-7}$cycloalkyl, CONHR$^5$, phenyl optionally substituted by R$^{10}$ and/or R$^{11}$, heteroaryl optionally substituted by R$^{10}$ and/or R$^{11}$ and heterocyclyl optionally substituted by R$^{10}$ and/or R$^{11}$, and
when r is 2, R$^8$ is additionally selected from C$_{1-6}$alkoxy, NHCOR$^5$, NHCONHR$^5$, NR$^5$R$^6$ and OH;
R$^9$ is selected from hydrogen, C$_{1-6}$alkyl, C$_{1-6}$alkoxy, —(CH2)$_s$—C$_{3-7}$ cycloalkyl, trifluoromethyl, —(CH$_2$)$_t$ phenyl optionally substituted by R$^{12}$ and/or R$^{13}$, —(CH$_2$)$_t$ heteroaryl optionally substituted by R$^{12}$ and/or R$^{13}$, —(CH$_2$)$_t$heterocyclyl optionally substituted by R$^{12}$ and/or R$^{13}$ and —(CH2)$_t$fused bicyclyl optionally substituted by R$^{12}$ and/or R$^{13}$;
R$^{10}$ is selected from C$_{1-6}$alkyl, C$_{1-6}$alkoxy, —CONR$^6$R$^{14}$, —NHCOR$^{14}$, —SO$_2$NHR$^{14}$, —NHSO$_2$R$^{14}$, halogen, trifluoromethyl, —X—$(CH_2)_j$-phenyl optionally substituted by one or more halogen atoms or $C_{1-6}$alkyl groups, —X—$(CH_2)_j$-heterocyclyl or —X—$(CH_2)_j$-heteroaryl wherein the heterocyclyl or heteroaryl group is optionally substituted by one or more substituents selected from $C_{1-6}$alkyl, $R^{11}$ is selected from $C_{1-6}$alkyl and halogen, or when $R^{10}$ and $R^{11}$ are ortho substituents, then together with the carbon atoms to which they are bound, $R^{10}$ and $R^{11}$ may form a five- or six-membered saturated or unsaturated ring to give a fused bicyclic ring system, wherein the ring that is formed by $R^{10}$ and $R^{11}$ optionally contains one or two heteroatoms selected from oxygen, nitrogen and sulfur;

$R^{12}$ is selected from $C_{1-6}$alkyl, $C_{1-6}$alkoxy, —$(CH_2)_s$—$C_{3-7}$cycloalkyl, —$CONR^{15}R^{16}$, —$NHCOR^{16}$, —$SO_2NHR^{15}$, —$NHSO_2R^{16}$, halogen, —$(CH_2)_k$$NR^{17}R^{18}$, oxy, trifluoromethyl, phenyl optionally substituted by one or more $R^{13}$ groups and heteroaryl wherein the heteroaryl is optionally substituted by one or more $R^{13}$ groups, $R^{13}$ is selected from $C_{1-6}$alkyl, $C_{1-6}$alkoxy, halogen, trifluoromethyl and —$NR^{17}R^{18}$, or $R^{12}$ and $R^{13}$, together with the carbon atoms to which they are bound, form a five- or six-membered saturated or unsaturated ring to give a fused bicyclic ring system, wherein the ring that is formed by $R^{12}$ and $R^{13}$ optionally contains one or two heteroatoms selected from oxygen, nitrogen and sulfur;

$R^{14}$ is selected from hydrogen and $C_{1-6}$alkyl;

$R^{15}$ is selected from hydrogen, $C_{1-6}$alkyl and phenyl wherein the phenyl group may be optionally substituted by one or more $R^{13}$ groups, $R^{16}$ is selected from hydrogen and $C_{1-6}$alkyl, or $R^{15}$ and $R^{16}$, together with the nitrogen atom to which they are bound, form a five- to six-membered heterocyclic ring optionally containing one additional heteroatom selected from oxygen, sulfur and N—$R^7$, wherein the ring is optionally substituted by up to two $C_{1-6}$alkyl groups;

$R^{17}$ is selected from hydrogen, $C_{1-6}$alkyl and —$(CH_2)_s$—$C_{3-7}$cycloalkyl optionally substituted by $C_{1-6}$alkyl, $R^{18}$ is selected from hydrogen and $C_{1-6}$alkyl, or $R^{17}$ and $R^{18}$, together with the nitrogen atom to which they are bound, form a three- to seven-membered heterocyclic ring optionally containing one additional heteroatom selected from oxygen, sulfur and N—$R^7$, wherein the ring may contain up to one double bond and the ring is optionally substituted by one or more groups;

$R^{19}$ is selected from $C_{1-6}$alkyl, oxy, —$CH_2OC_{1-6}$alkyl, trichloromethyl and —$N(C_{1-6}alkyl)_2$;

X is selected from —O— and a bond;

U is selected from methyl and halogen;

W is selected from methyl and chlorine;

V and Y are each selected independently from hydrogen, methyl and halogen;

m is selected from 1, 2, 3 and 4, and wherein at least one carbon atom of the resulting carbon chain is substituted with one or two groups selected independently from a $C_{1-6}$alkyl substituted with one to three OH groups;

n, p, r and j are independently selected from 0, 1 and 2;

q and k are independently selected from 0, 1, 2 and 3; and s and t are independently selected from 0 and 1;

or a pharmaceutically acceptable derivative thereof.

\* \* \* \* \*